(12) United States Patent
Varshney et al.

(10) Patent No.: US 7,009,033 B2
(45) Date of Patent: Mar. 7, 2006

(54) HETEROFUNCTIONAL POLYETHYLENE GLYCOL AND POLYETHYLENE OXIDE, PROCESS FOR THEIR MANUFACTURE

(75) Inventors: Sunil K. Varshney, Pointe-Claire (CA); Jian Xin Zhang, Dorval (CA)

(73) Assignee: Polymer Source Inc., Dorval (CA)

( * ) Notice: Subject to any disclaimer, the term of this patent is extended or adjusted under 35 U.S.C. 154(b) by 664 days.

(21) Appl. No.: 09/895,323

(22) Filed: Jul. 2, 2001

(65) Prior Publication Data

US 2003/0027929 A1 Feb. 6, 2003

(51) Int. Cl.
*C08G 65/28* (2006.01)
*C08G 65/332* (2006.01)

(52) U.S. Cl. .................. 528/421; 524/612; 528/405

(58) Field of Classification Search ............... 528/421
See application file for complete search history.

(56) References Cited

U.S. PATENT DOCUMENTS

| 5,672,662 | A | * | 9/1997 | Harris et al. ............... 525/408 |
| 5,929,177 | A | * | 7/1999 | Kataoka et al. ............ 525/408 |
| 6,730,334 | B1 | * | 5/2004 | Zhao ..................... 424/78.3 |
| 2005/0025821 | A1 | * | 2/2005 | Harvie et al. ............. 424/450 |

OTHER PUBLICATIONS

Zalipsky, "Functionalized Poly(ethylene glycol) for Preparation of Biologically Relevant Conjugates," Bioconjugate Chem., vol. 6, 1995, pp. 150-165.*
Zalipsky et al., "Facile synthesis of alpha-hydroxy-omega-carboxymethylpolyethylene oxide," Journal of Bioactive and Compatible Polymers, vol. 5, Apr. 1990, pp. 227-231.*
CAPLUS accession No. 1978:51198 for the Makromolekulars Chemie article by Broze et al., "Some noew easy routes for the specific functionalization of polymers by pendant or end amino groups," vol. 178, No. 11, 1977.*
CAPLUS accession No. 2000:217495 for the Gaofenzi Tongbao article by Xiong et al., "Progress in synthesis of polyethylene glycol derivatives," vol. 1, 2000.*

* cited by examiner

*Primary Examiner*—Robert Sellers
(74) *Attorney, Agent, or Firm*—Bereskin & Parr

(57) ABSTRACT

Heterofunctional polyethylene glycol or polyethylene oxide, represented by one of the following formula (I) to (IV):

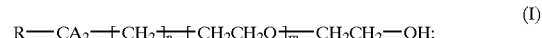
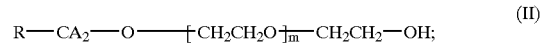
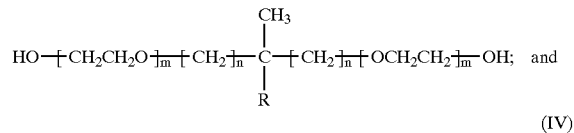
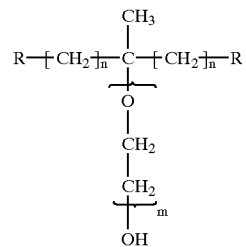

wherein:
m is an integer from 5 to 10,000;
n is an integer from 1 to 20;
each R is independently an organic substituent, preferably an hydrocarbon substituent that preferably comprises at least one heteroatom,
each A is independently an alkyl, a substituted alkyl group or an hydrogen atom,
and the salts thereof.

9 Claims, 21 Drawing Sheets

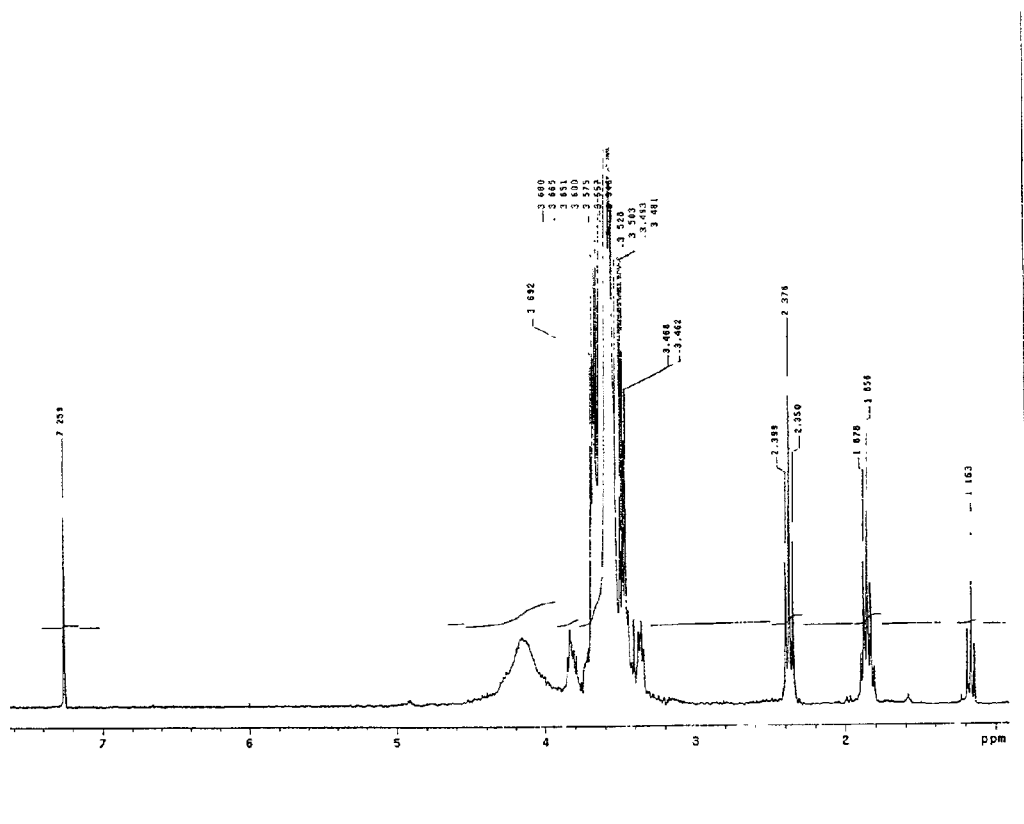
Figure 1. Proton NMR spectrum of α-carboxylic-ω-hydroxyl polyethylene oxide (Run P2243)

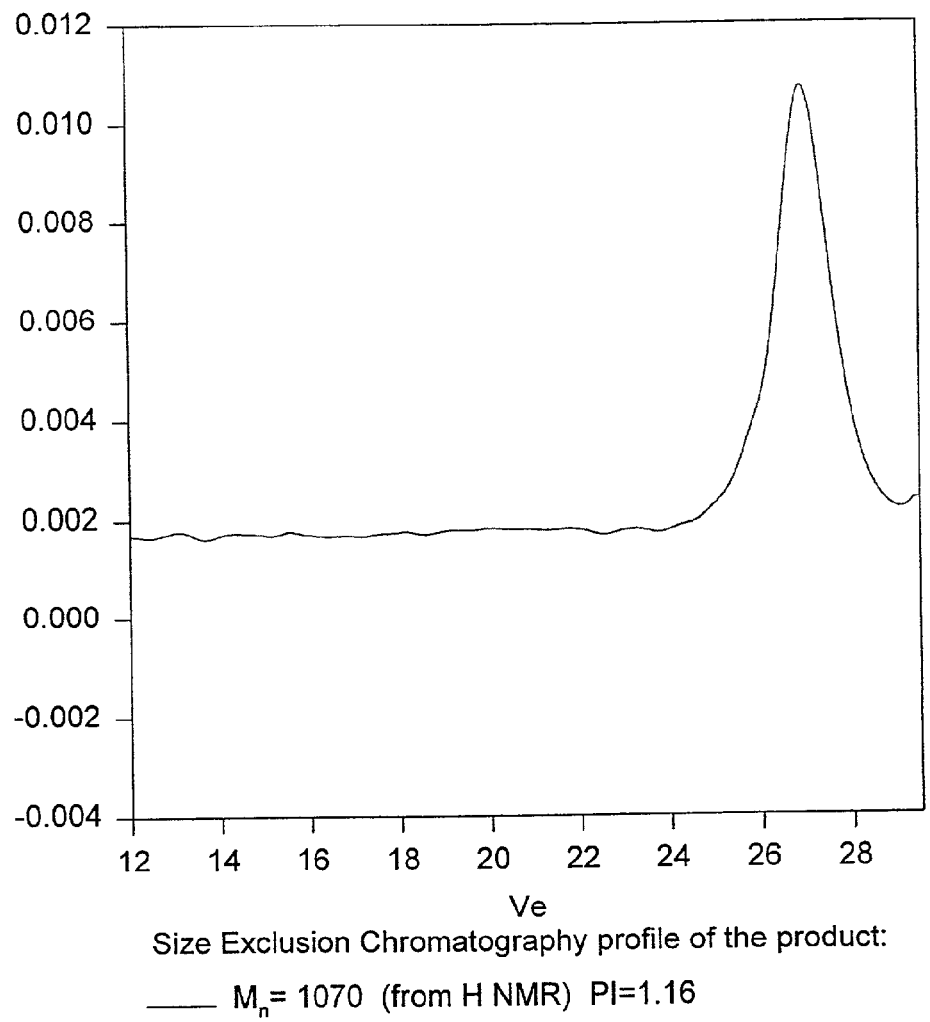
Figure 2. SEC profile of α-carboxylic-ω-hydroxyl polyethylene oxide (Run P2243)

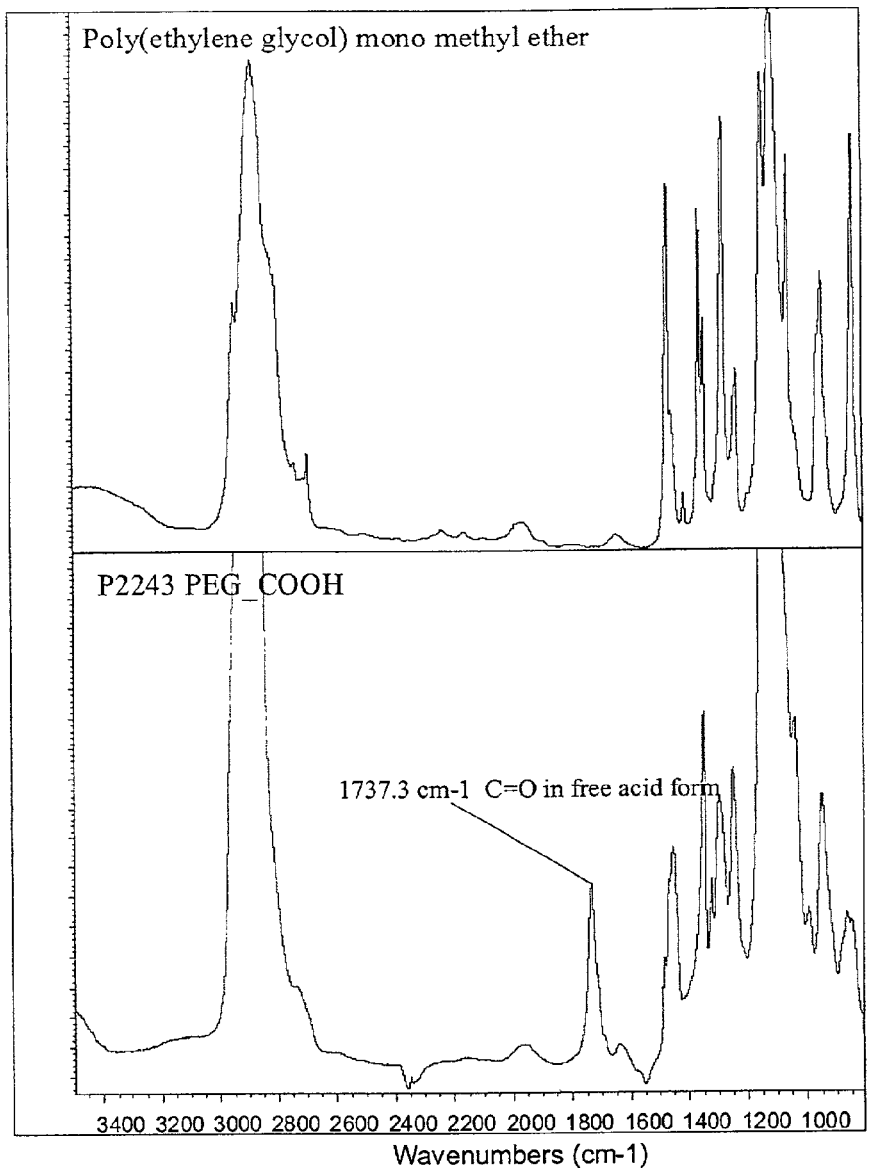
Figure 3. FT-IR spectrum of α-carboxylic-ω-hydroxyl polyethylene oxide (Run P2243) Comparing to that of α-methoxyl-ω-hydroxyl polyethylene oxide.

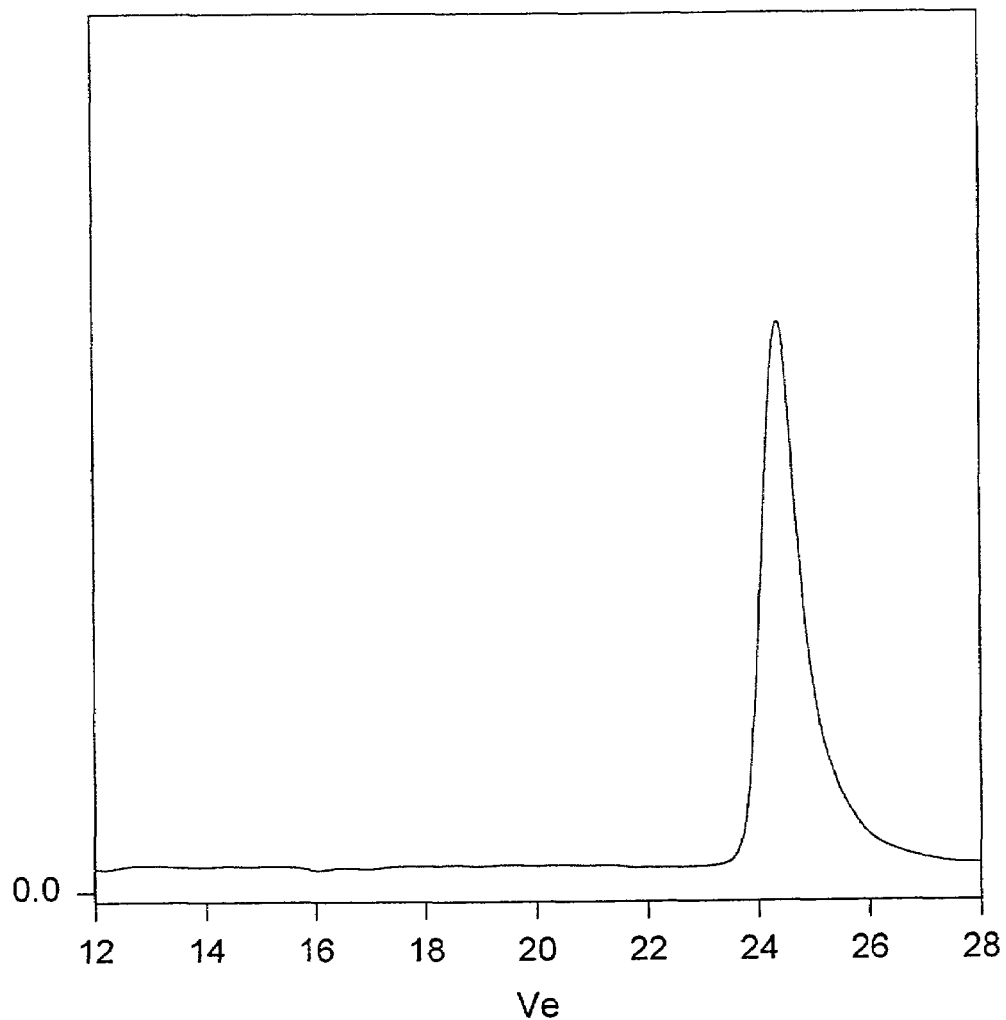
Figure 4. SEC profile of α-carboxylic-ω-hydroxyl polyethylene oxide (Run P2264)

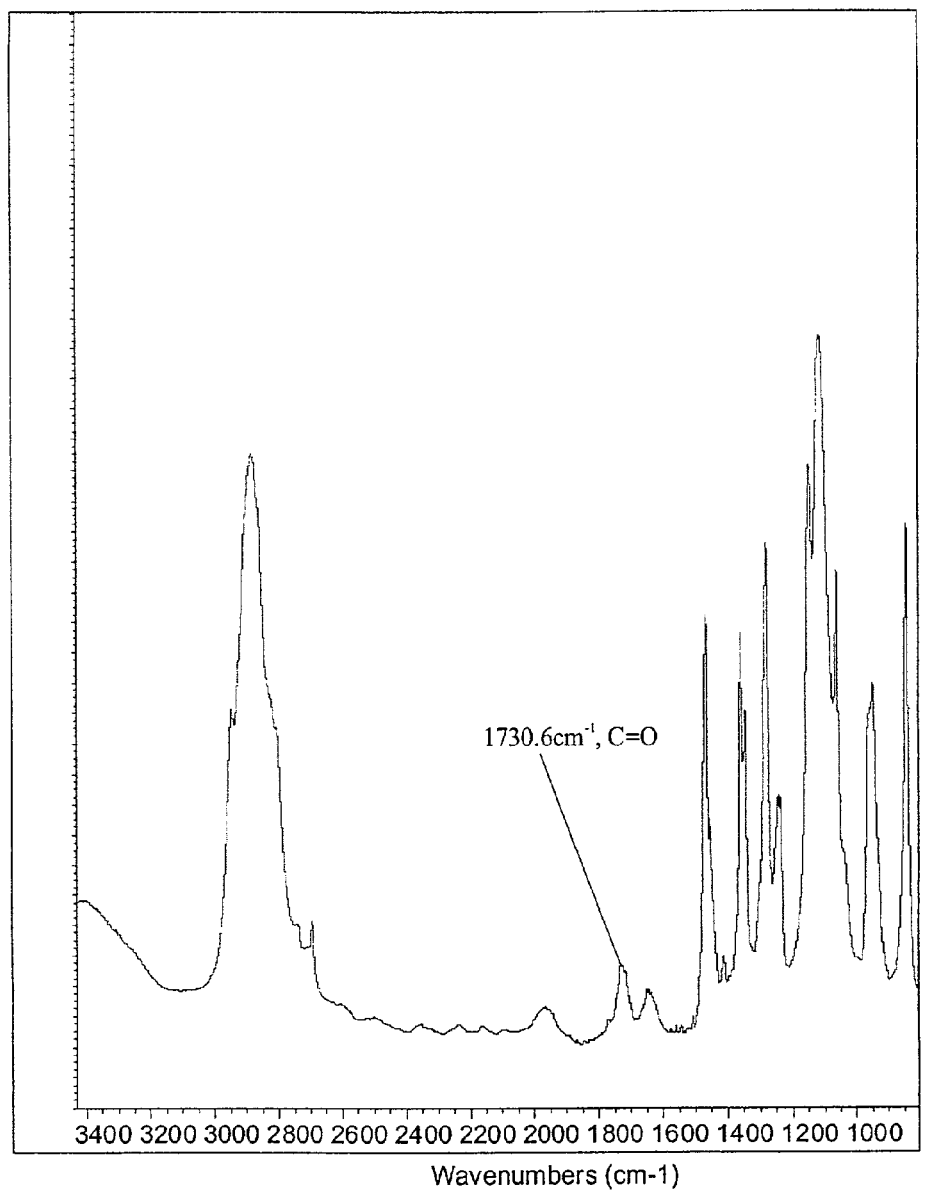
Figure 5. FT-IR spectrum of α-carboxylic-ω-hydroxyl polyethylene oxide (Run P2264)

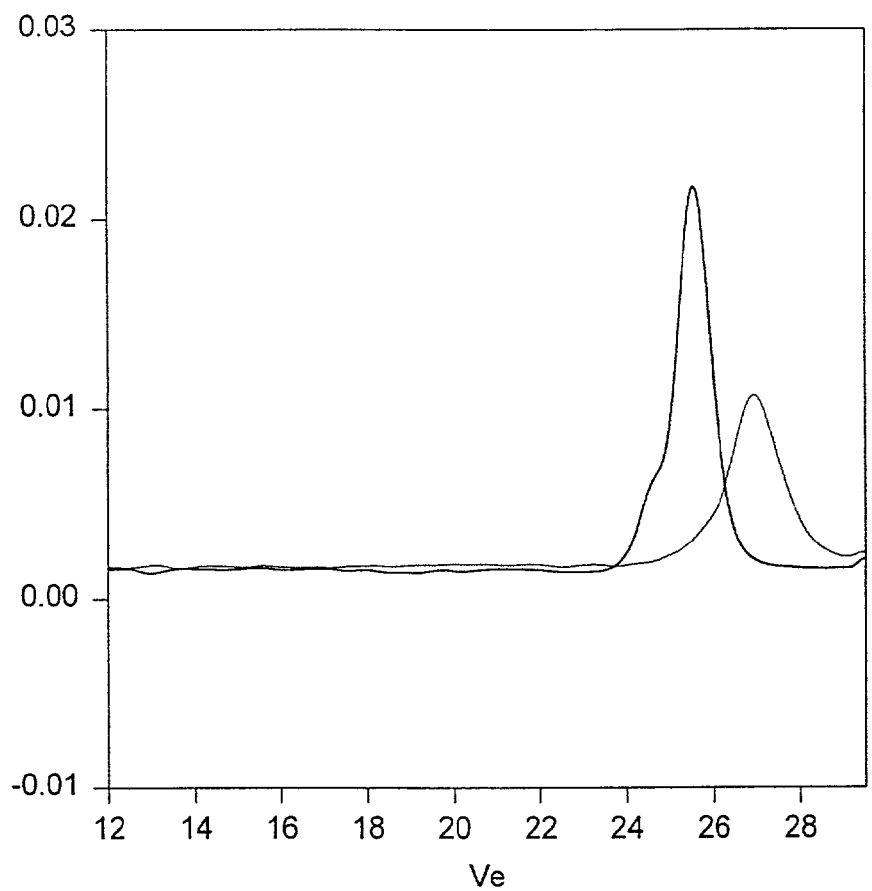
Figure 6. SEC profile of α-carboxylic-ω-hydroxyl polyethylene oxide (Run P2263)

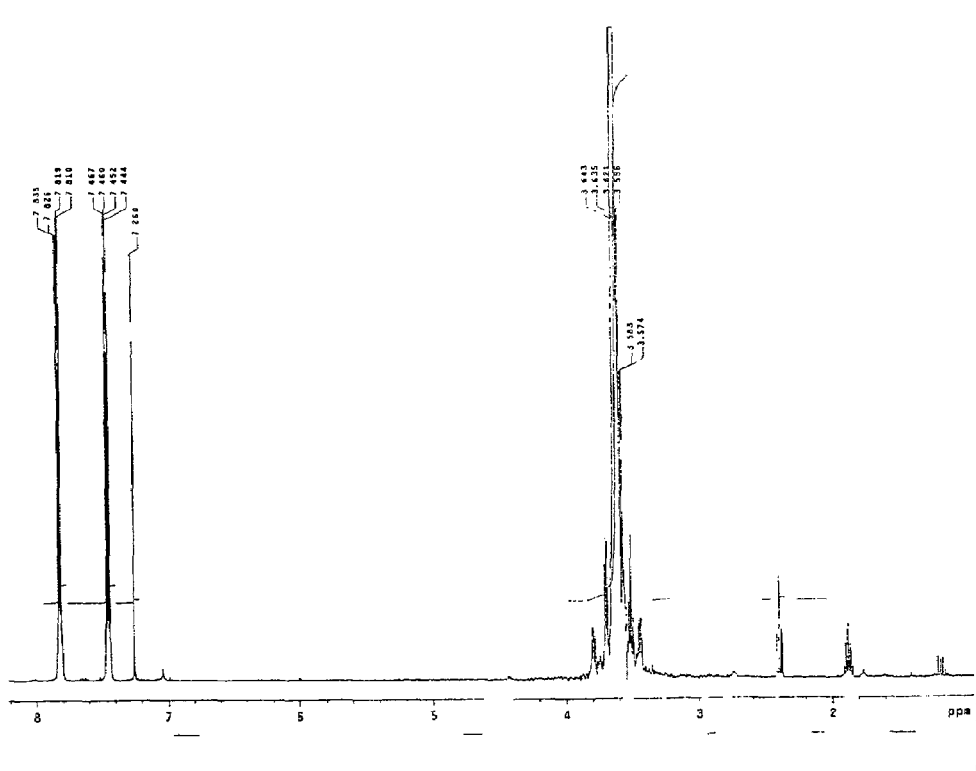
Figure 7. Proton NMR spectrum of α-carboxylic-ω-hydroxyl polyethylene oxide (Run P2263)

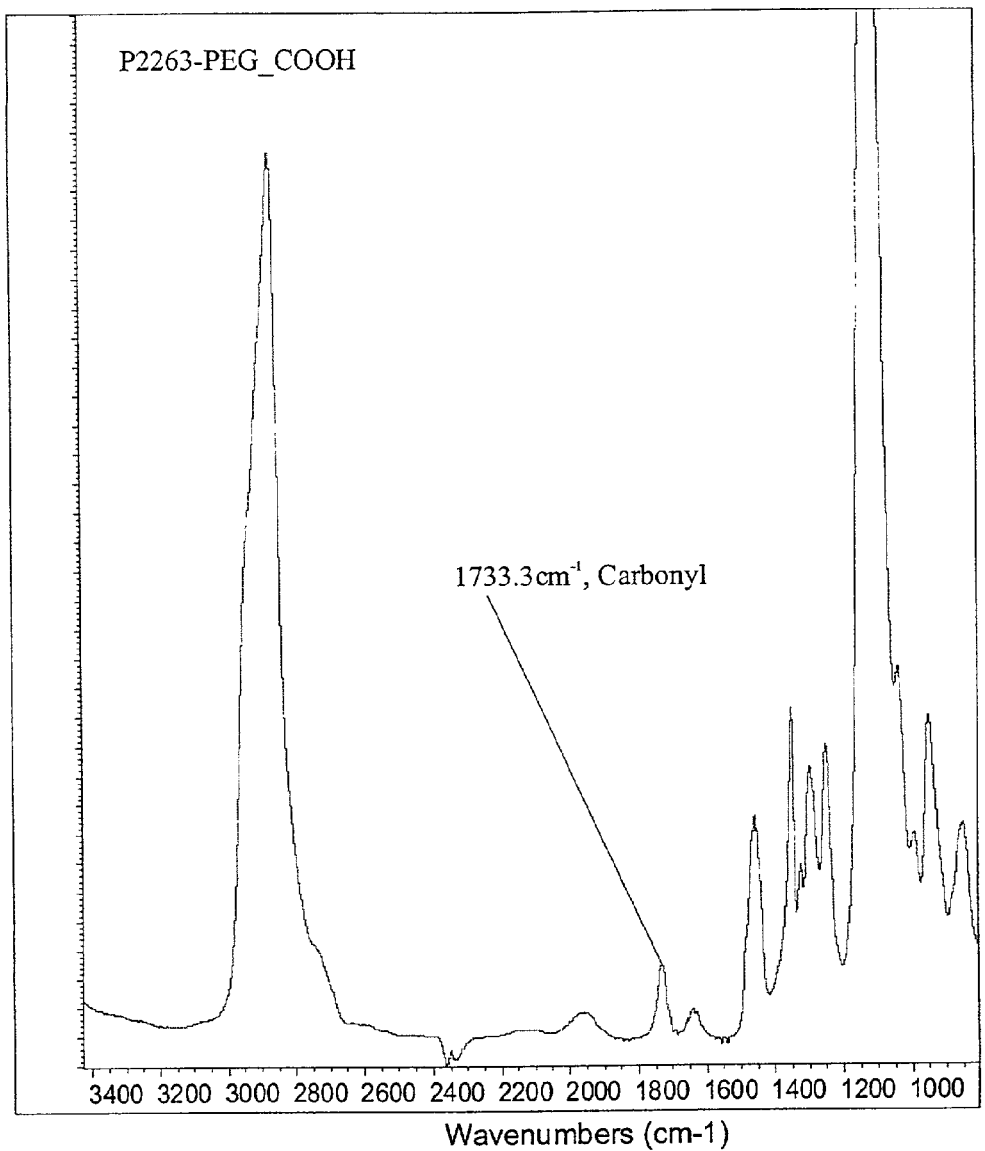
Figure 8. FT-IR spectrum of α-carboxylic-ω-hydroxyl polyethylene oxide (Run P2263)

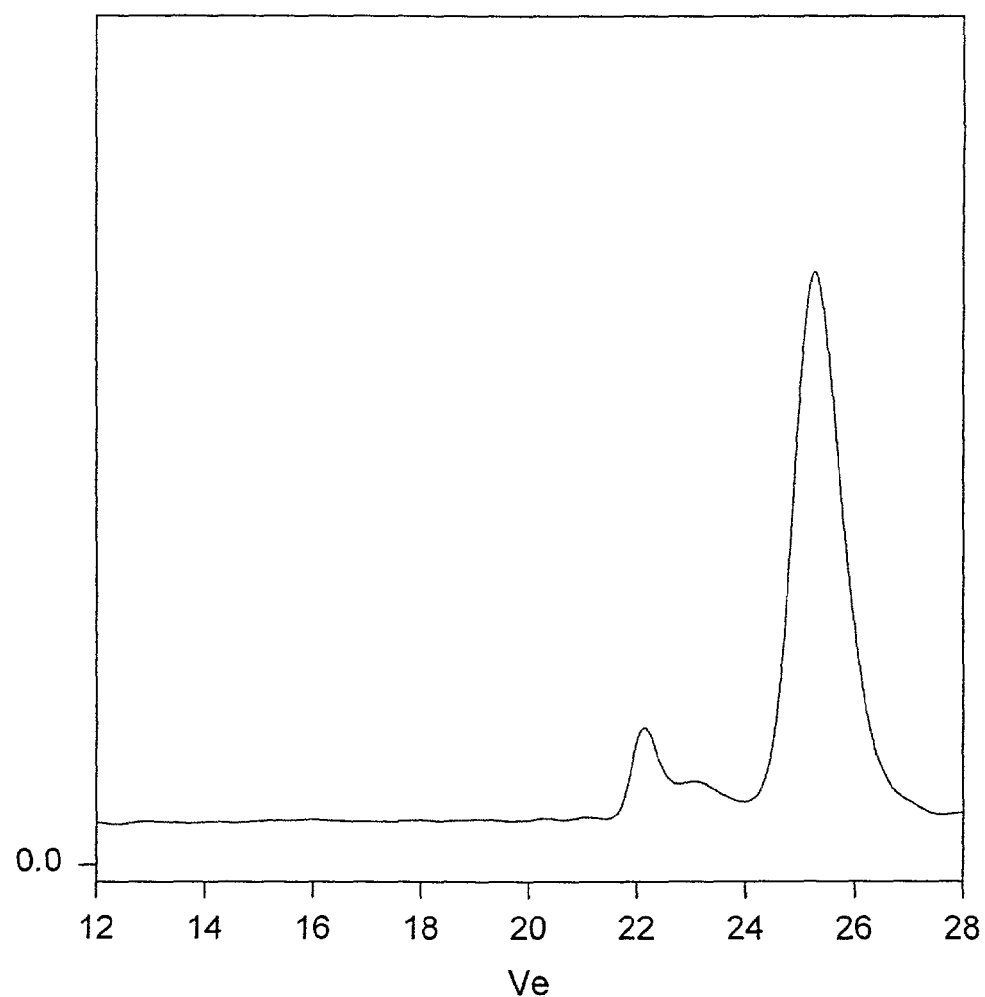
Figure 9. SEC profile of α-carboxylic-ω-hydroxyl polyethylene oxide (Run P2418)

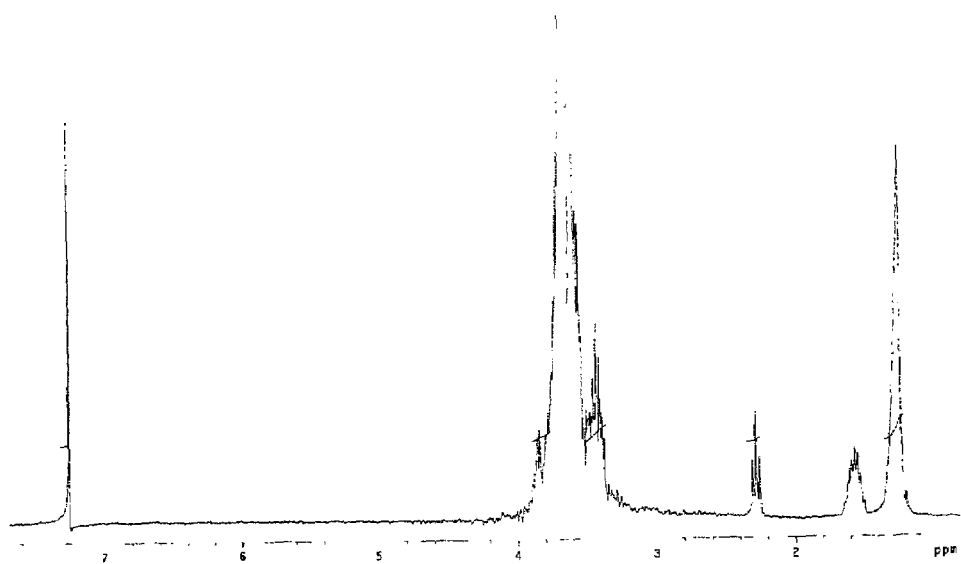
Figure 10. H NMR spectrum of α-carboxylic-ω-hydroxyl polyethylene oxide (Run P2418)

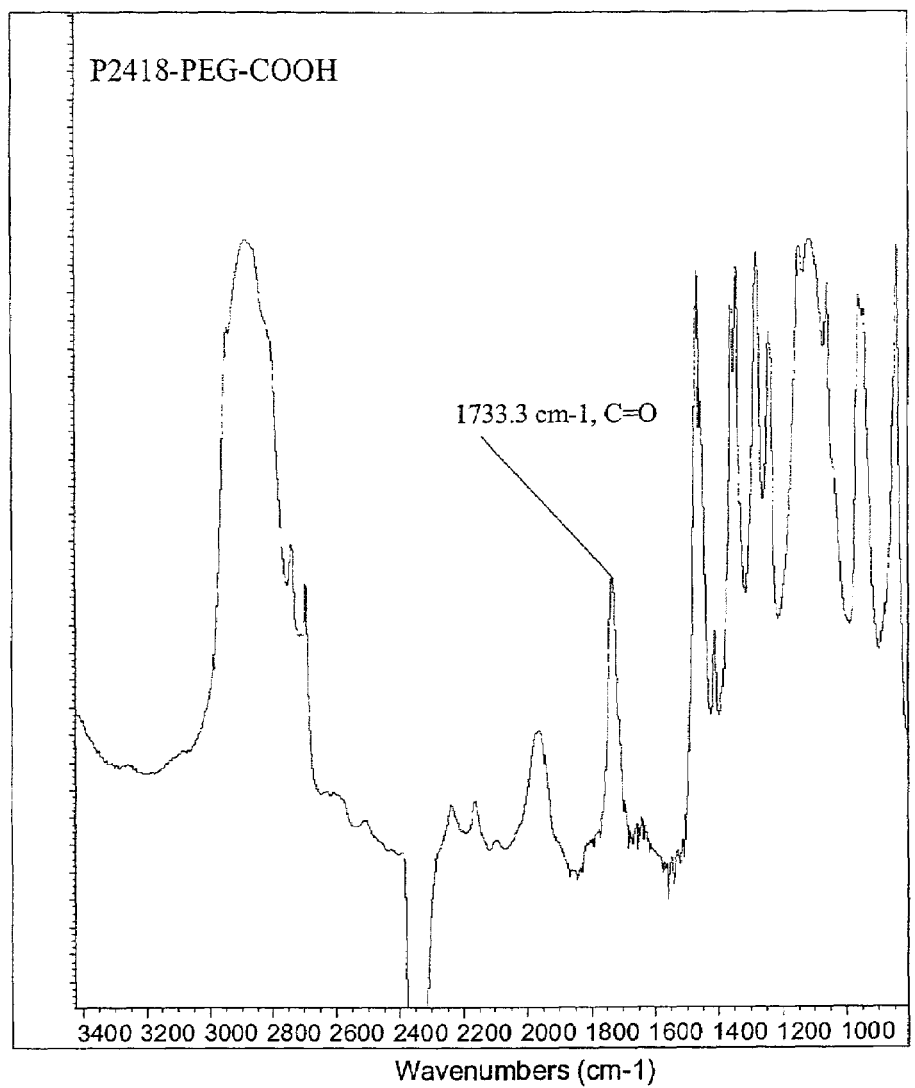
Figure 11. FT-IR spectrum of α-carboxylic-ω-hydroxyl polyethylene oxide (Run P2418)

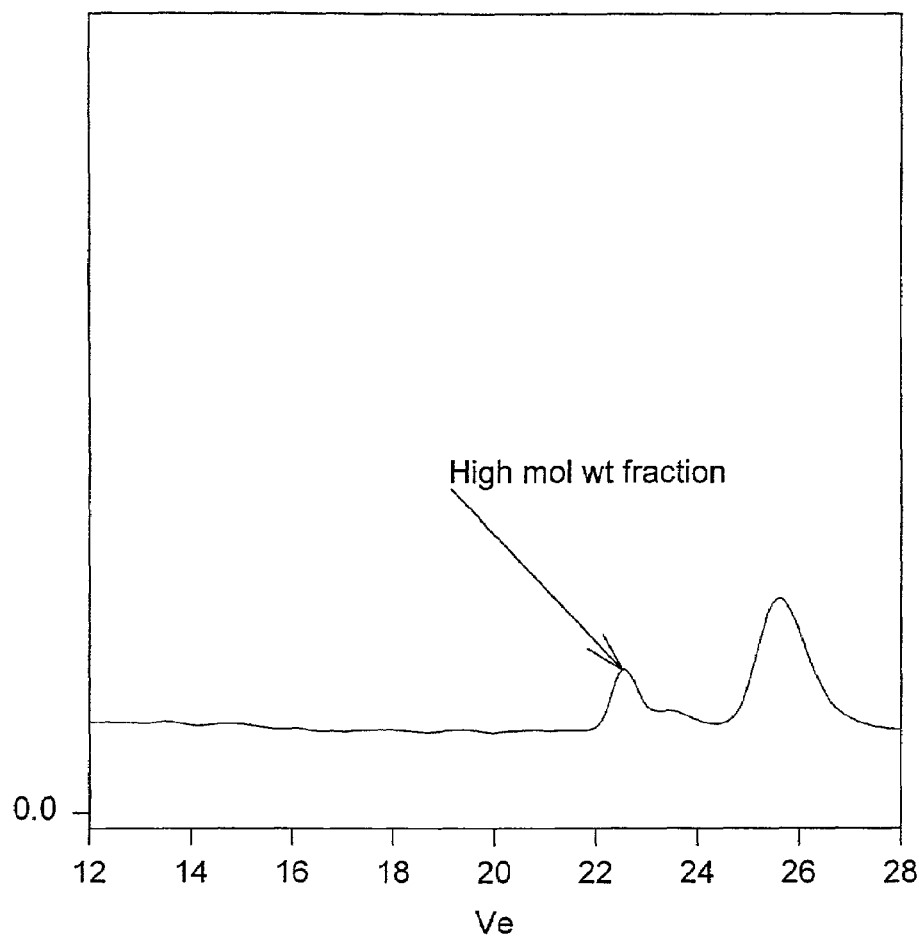
Figure 12. SEC profile of α-carboxylic-ω-hydroxyl polyethylene oxide (Run P2420), which shows the bimodal distribution.

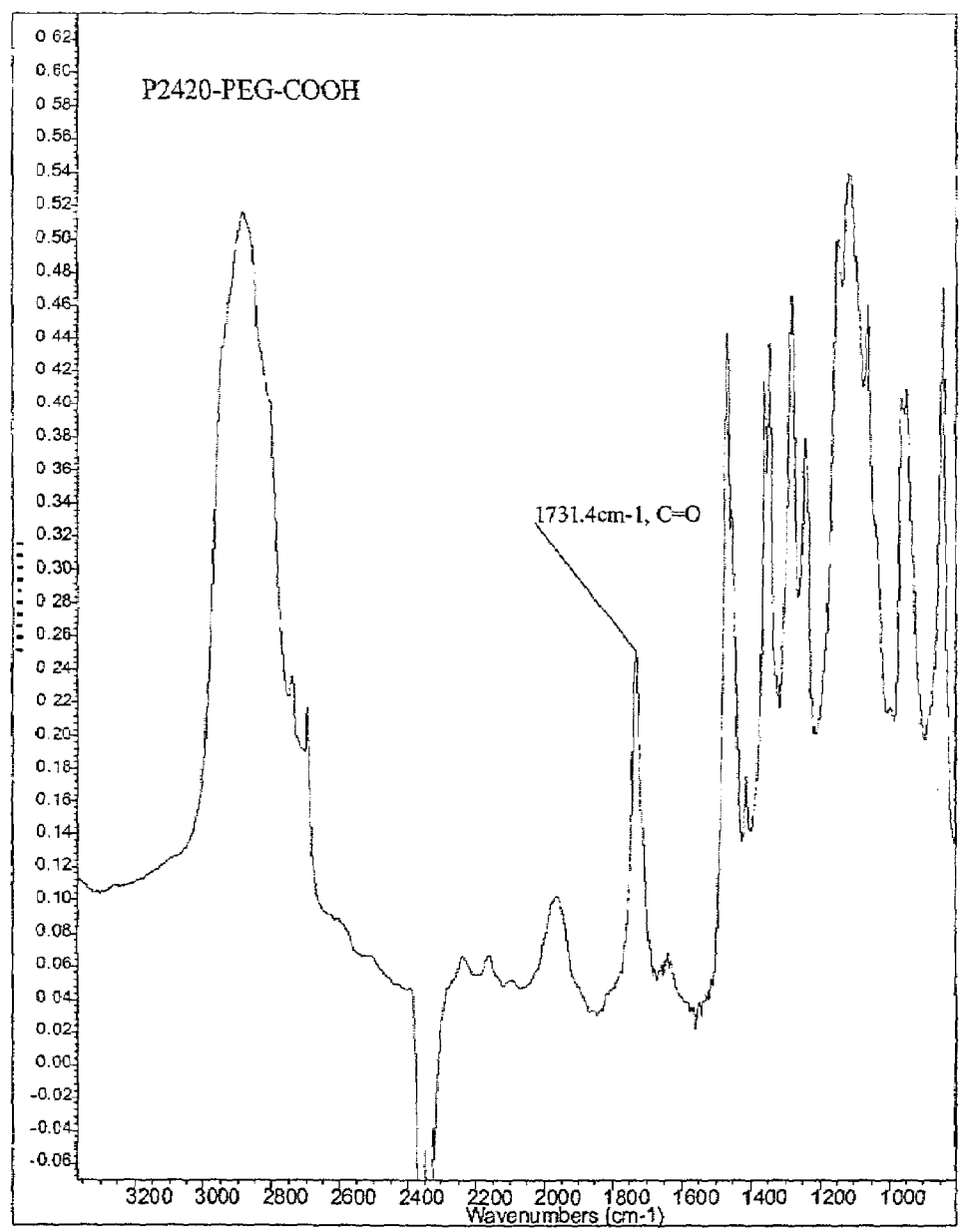
Figure 13. FT-IR spectrum of α-carboxylic-ω-hydroxyl polyethylene oxide (Run P2420)

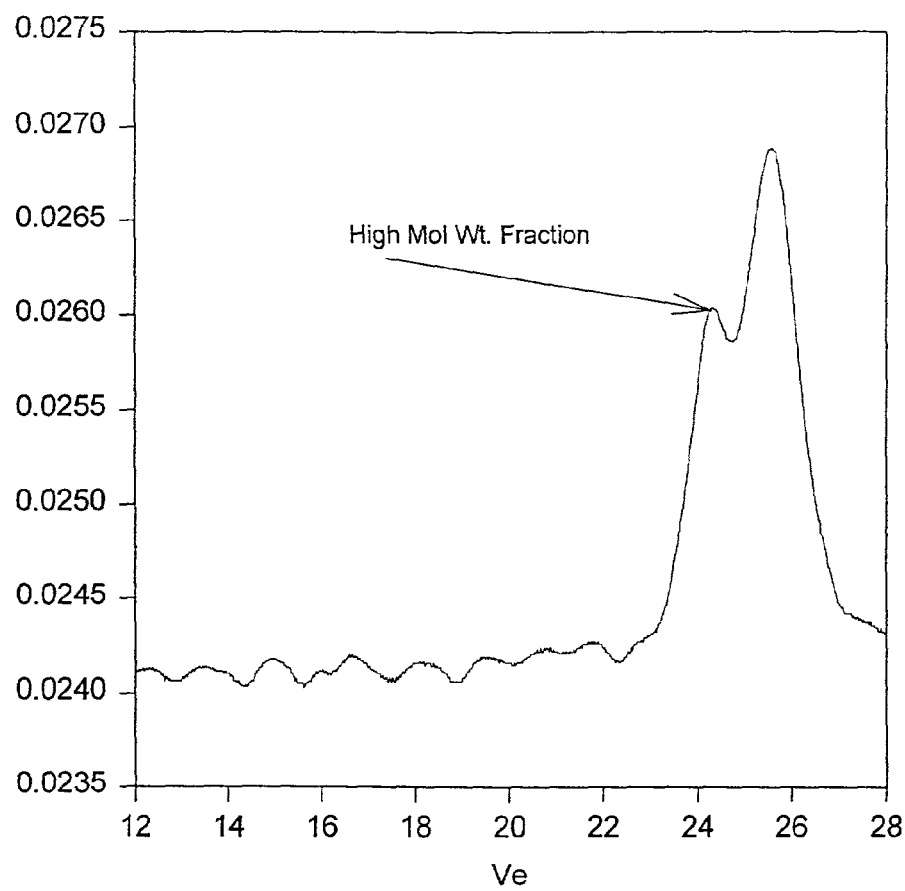
Figure 14. SEC profile of α-carboxylic-ω-hydroxyl polyethylene oxide (Run P2423), Bimodal distribution was observed.

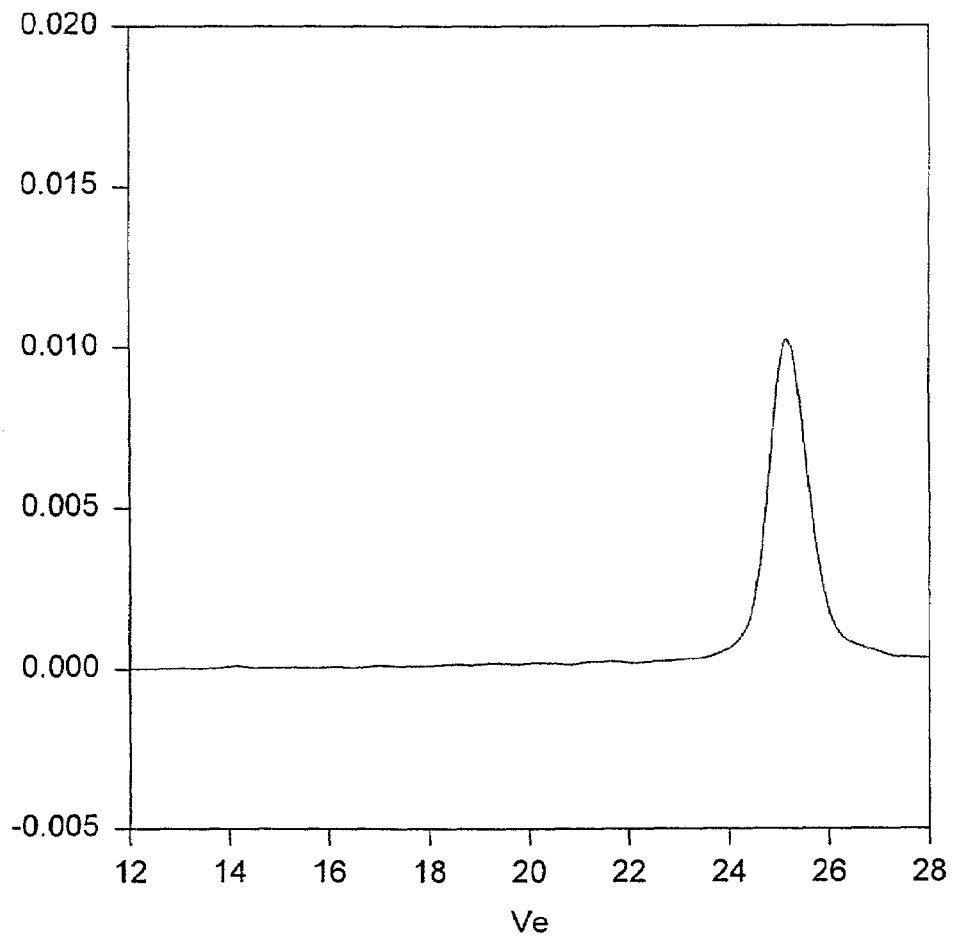
Figure 15. SEC profile of α-carboxylic-ω-hydroxyl polyethylene oxide (Run P2622)

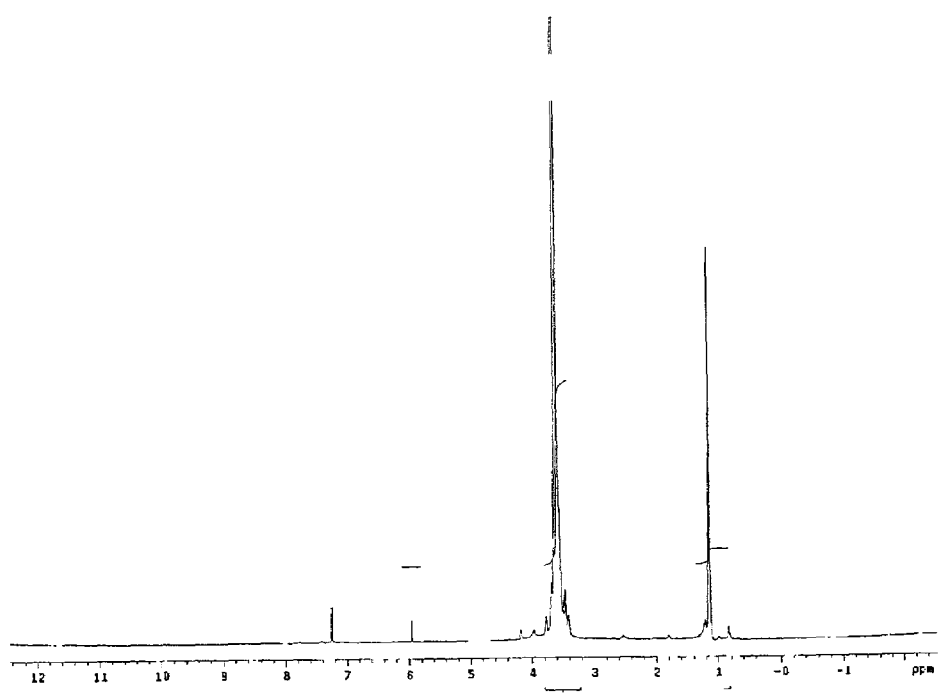
Figure 16. H NMR spectrum of α-carboxylic-ω-hydroxyl polyethylene oxide (Run P2622)

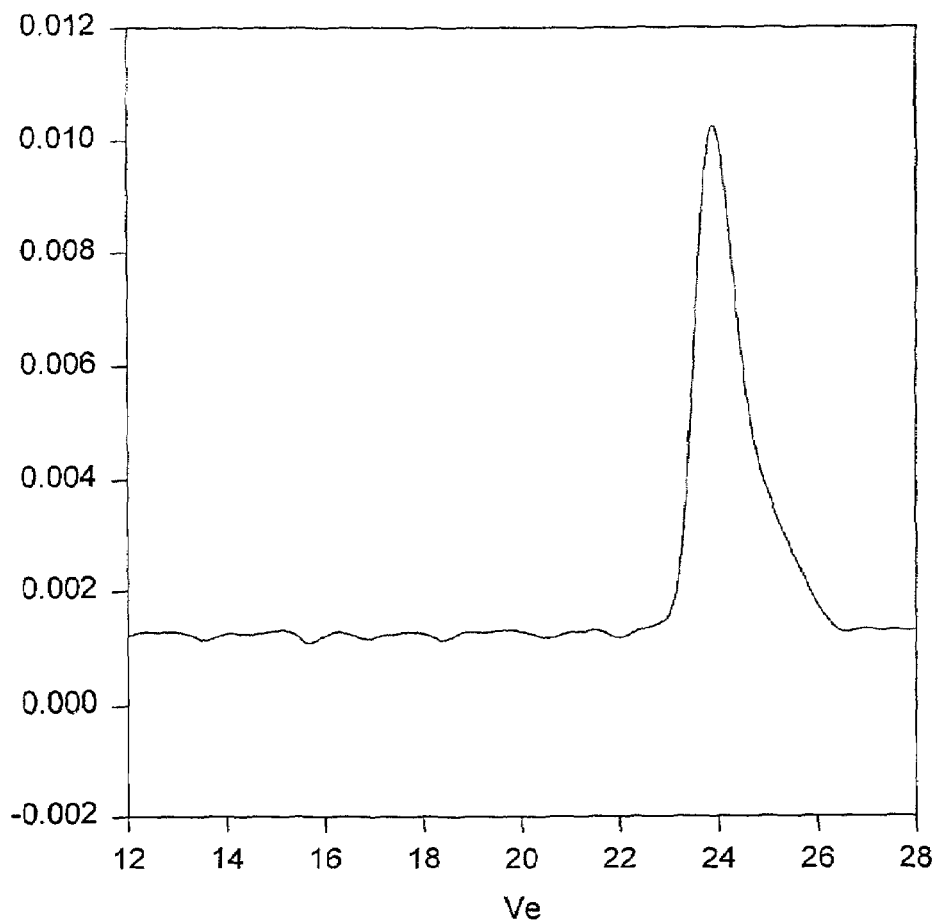
Figure 17. SEC profile of α-carboxylic-ω-hydroxyl polyethylene oxide (Run P2627)

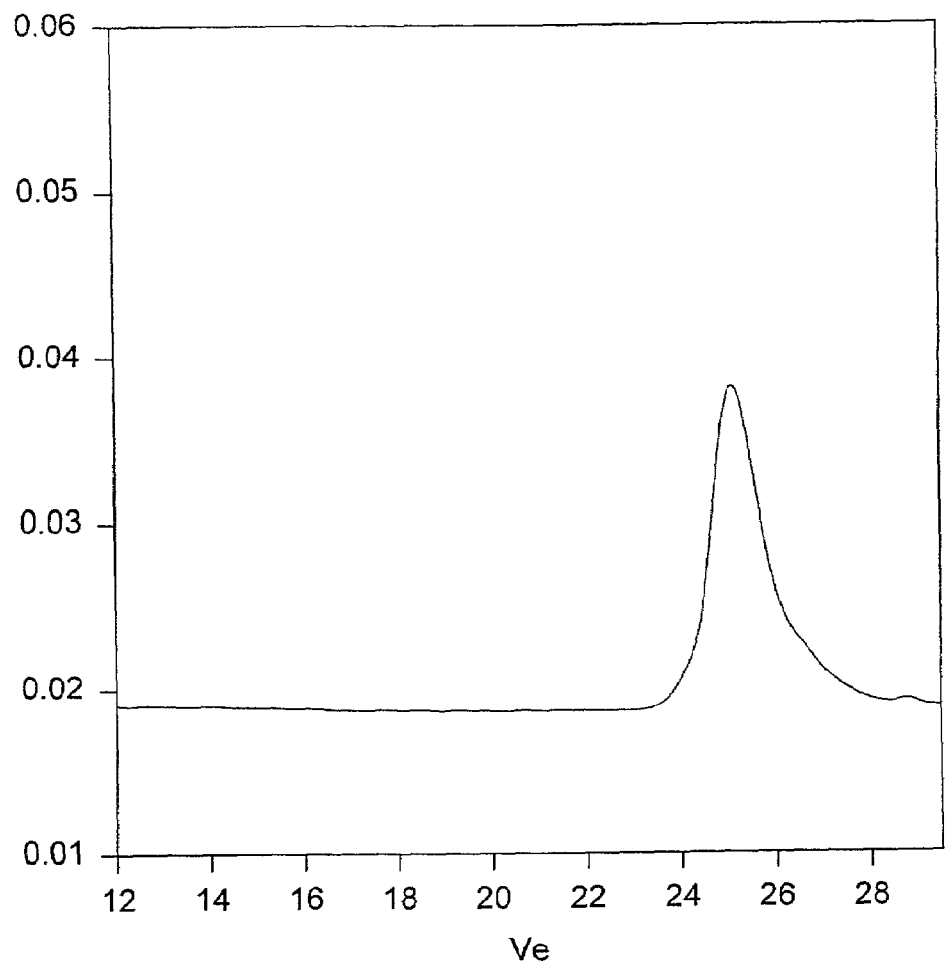
Figure 18. SEC profile of α-carboxylic-ω-hydroxyl polyethylene oxide (Run P2425)

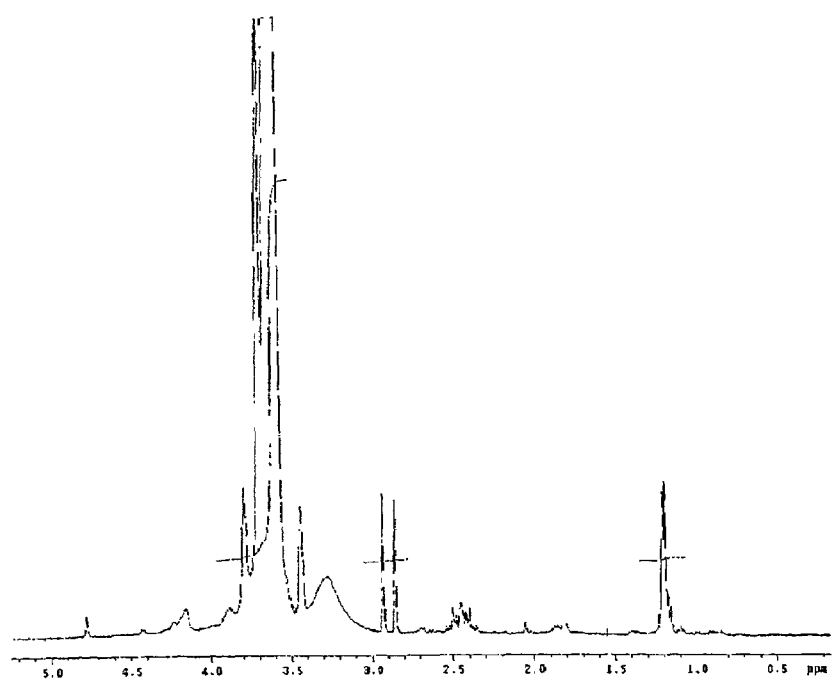
Figure 19. H NMR spectrum of α-carboxylic-ω-hydroxyl polyethylene oxide (Run P2425)

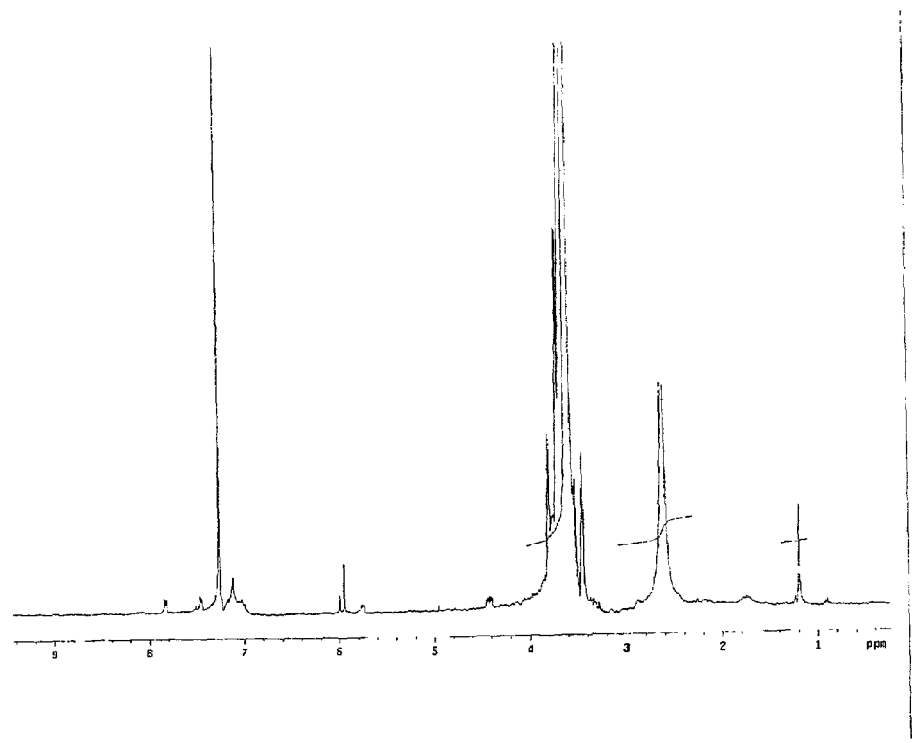
Figure 20. H NMR spectrum of α,ω-dihydroxy polyethylene glycol bearing carboxylic acid functional moiety at the backbone of polymer chain (Run P2625)

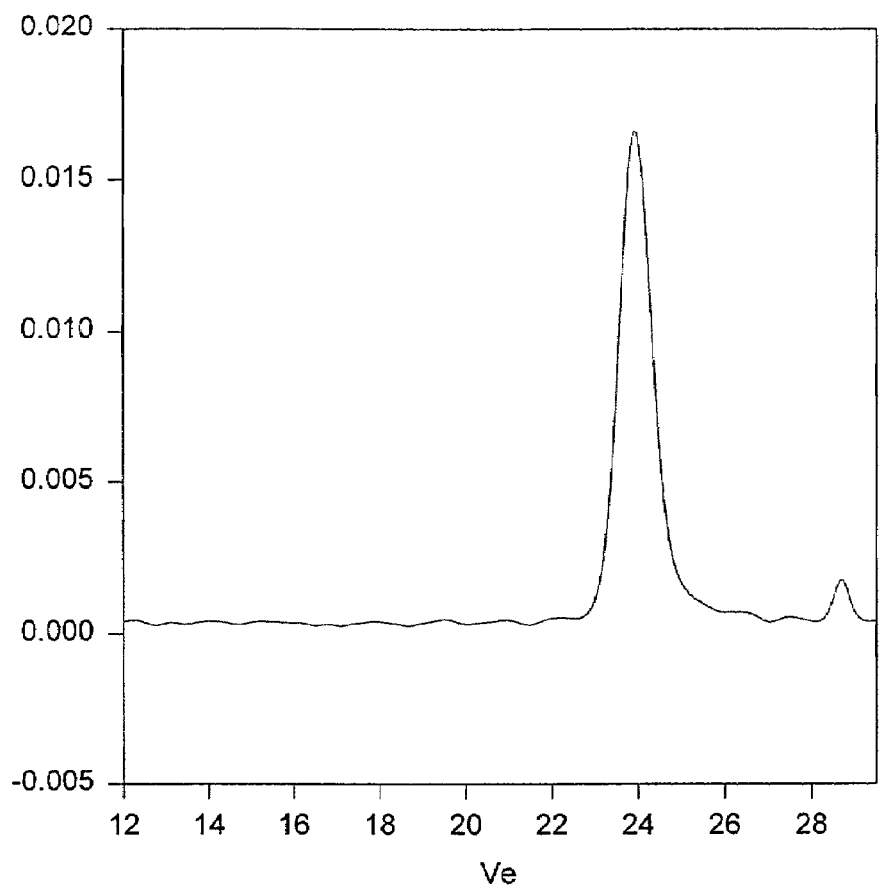
Figure 21. SEC profile of α,ω-dihydroxy polyethylene glycol bearing carboxylic acid functional moiety at the backbone of polymer chain (Run P2625)

HETEROFUNCTIONAL POLYETHYLENE GLYCOL AND POLYETHYLENE OXIDE, PROCESS FOR THEIR MANUFACTURE

BACKGROUND OF THE INVENTION

The ring opening polymerization of ethylene oxide cyclic monomer obtains polyethylene glycol or polyethylene oxide. Ethylene oxide or various epoxides, and other cyclic ethers can be polymerized with anionic, cationic, and coordination type catalyst. For the commercial production of polymer of such type, the most effective catalyst found were $(CH_3)_3N$, Na, K, and $SnCl_4$, $CaCO_3$, $FeCl_3$. The other compounds showing catalytic activity were $NaNH_2$, ZnO, SrO and CaO. The resulting polymer bears the following chemical structure:

The control polymerization of ethylene oxide can be achieved by aqueous alkali as catalyst. The monomer conversion increase linearly with time and that the degree of polymerization (and molecular weight) increased as the reaction proceeded.

Based on the number of repeat units the polymer normally known as poly(ethylene glycol) (PEG) or poly(ethylene oxide) (PEO). If 'm' is lower than 455 and the terminal ends of the polymer chain bears hydroxyl group than the polymer term as polyethylene glycol. This formula can be represented in brief as:

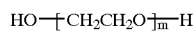

or if the chemical structure are as

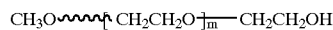

than it is called polyethylene glycol mono methylether, or mPEG in brief, in which one terminus is the relatively inert bearing methoxy group ($OCH_3$), while the other terminus is a hydroxyl group can be modified to other functional group such as amino, halogen, sulfonic acid, carboxylic acid etc. Similarly, other alkyloxy groups such as benzyloxy ($CH_2$—$C_6H_5$), tert-butoxy ($C(CH_3)_3$ ethoxy ($OCH_2CH_3$) or any long chain branch or linear alkyloxy can be substituted for methoxy in the above formula.

When a linear or branched polymer's chain ends are functionalized that participate in further chain extension referred as Macromonomers and Telechelics. They are normally low molecular weight polymers and can be distinguished from one another by the functionality of their chain ends, and by the nature of the products resulting from the reactions of their chains ends. The term macromonomer or macromer, (i.e., macromolecular monomer) was introduced by Milkovich in 1974, and can be defined as oligomers or polymers having at least one homopolymerizable end group. Such groups may be either vinylic, acetylenic, acrylic or heterocyclic. The term telechelic is derived from the Greek word 'tele'=distant and 'chelos'=claw. This term was proposed by Uraneck, and can be defined as relatively low molar mass macromolecules possessing two reactive end groups. A polymer or oligomer can be considered to be a telechelic if it contains at least one reactive end group that can react selectively to give a bond with another molecule. Depending on functionality, telechelics can be classified as mono, di-, tri-, or poly-telechelic. Similarly when a difunctional carboxylic or sulfonic acid terminated polymer chains are converted to a salt form by neutralization with metal alkoxides in appropriate solvents, the polymers are refer to halato-telechelics as reported by Teyssie. These functionalized polymer bearing functional group at both terminus are normally termed as telechelics and if the one end of the polymer chain is functionalized, it is term as monochelics.

The telechelic polymers can be obtained by "living" anionic or cationic polymerization, or even by stable free-radical process. The living polymerization techniques are unequivocally preferred to other methods in order to control their molecular parameters: molecular weight, homogeneity of each chain length, i.e. low molecular dispersity, microstructure of the polymer backbone, and finally, nature of the end group of the chain. By controlling such parameters, these properly tailored macromolecules can then be used to design new polymeric materials. The end functionalization can be achieved by two different strategies: (1) Either by deactivation of the living species with a suitable electrophile or chain transfer reagent or (2) By initiation of the living process with an organic anionic species that bears the protected functionalized group. However, a disadvantage in the former route to prepare functionalized polymer is that any polymer chain that has been terminated during the propagation will not react with the electrophile, therefore, impairing quantitative functionalization. If such conventional procedures are not available, end functionalized polymer can however be obtained in high yield by appropriate chemical modification of a existing reactive functional group available on the polymer chain. In any event, the functionalization with functional group must be as quantitative as possible for further use of the products. Polymerization of ethylene oxide can be carried out in solvent with high polarity solvent such as tetrahydrofuran (THF), N,N'-dimethylformamide (DMF), methyl sulfoxide (DMSO) etc. The initiator can be alkali metal based compounds such as Na, K, Cs etc. However one can achieved the polymerization of ethylene oxide using lithium based initiator if the polymerization is carried out in the presence of phosphazene base t-$BuP_4$ at 40° C. polymerization temperature.

Branched PEGs architecture are also known. The branched architecture can be synthesized by addition of ethylene oxide to various multifunctional initiator such as potassium salt of polyols that includes glycerol, pentaerythritol, dipentaerythritol, sorbitol or multifunctional polyols etc. These polyols generate three-, four-, six-, eight-, or multi-arm branched PEG respectively. The architecture of these branched polymer can be illustrated as shown below:

in which core represents a central core based on the initiator polyol molecule and x represents the number of arms which can range from 3, 4, 6, 8 or more. The terminal hydroxyl groups are readily subject to further chemical modification as desired. Wherein core is a branching core moiety and x is from 3 to about 100 or more. Star like polymers are generally described in U.S. Pat. No. 5,171,264 to Merrill. A branched form of PEG and related polymers is also described in recent patent application U.S. Ser. No. 08/443,383. The branched form has a single terminus per branch that can be chemically modified to other various functional group such as NH$_2$ or COOH, SO$_3$H etc.

The copolymers of ethylene oxide and propylene oxide are closely related to PEG in their chemistry, and they can be substituted for PEG in many of its applications.

R = H or CH3

Poly(ethylene glycol) is used in biological applications because it has properties that are highly desirable and is generally approved for biological or biotechnical applications. PEG is clear, colorless, odorless, soluble in water, stable to heat, inert to many chemical agents, does not hydrolyze or deteriorate, and is nontoxic. Poly(ethylene glycol) is considered to be bio-compatible, which is to say that PEG is capable of coexistence with living tissues or organisms without causing harm. More specifically, PEG is not immunogenic, which is to say that PEG does not tend to produce an immune response in the body. When attached to a moiety having some desirable function in the body, the PEG tends to mask the moiety and can reduce or eliminate any immune response so that an organism can tolerate the presence of the moiety.

End-reactive poly(ethylene glycol)s (PEG) are very important class of material in a variety of fields such as biology, biomedical science, and surface chemistry, due to their unique properties such as solubility and flexibility of the chains and basicity of the ether oxygens in the main chain. It is a non-ionic water-soluble polymer. Non-toxic, it has been proven to resist recognition by immune system as well as to display resistance to protein and cell adsorption. These unique properties conjugated to chain flexibility and basicity of the ether oxygen atoms made it eligible for use in a variety of fields such as biology, biomedical science, and surface chemistry.

The effective functionalization of poly(ethylene oxide) chain-end leading to end-reactive polymer become more and more important due to the high versatility of the introduced end groups. One of the most important utilizations of PEG is the construction of polymer brushes, a densely packed layer of tethered polymers anchored on the surface utilizing the end-functionality of the polymer chain. Such a PEG brush significantly changes the surface properties. For example, a PEGylated surface, which means that the poly(ethylene glycol) chains are densely packed on a surface and attached by the end of the polymer chain, shows effective rejection of protein adsorption resulting in a good blood compatibility. In general, commercially available methoxy-ended PEGs having a hydroxyl group at the another terminus are utilized as the starting material for the monochelic PEG preparations. Thus, these PEG surface brushes possess inert free end groups (OCH3 terminal ends). If certain reactive groups can be introduced to the free ends of the brush, an opportunity for the PEG brush will be expanded. For example, the introduction of an affinity ligand to the brush free end changes the surface to be utilized for affinity separation, keeping a low nonspecific adsorption. When PEG is chemically attached to a water insoluble compound, the resulting conjugate generally is water soluble as well as soluble in many organic solvents. When the molecule to which PEG is attached is biologically active, such as a drug, this activity is commonly retained after attachment of PEG and the conjugate may display altered pharmacokinetics. For example, it has been demonstrated that the water insoluble antimalarial, artemisinin, becomes water soluble and exhibits increased antimalarial activity when coupled to PEG. (for example see the report published by Bentley et al., Polymer Preprints, 38(1):584 (1997). Furthermore, U.S. Pat. No. 4,179,337 to Davis et al. discloses that proteins coupled to PEG have enhanced blood circulation lifetime because of reduced kidney clearance and reduced immunogenicity. The lack of toxicity of the polymer and its rapid clearance from the body are advantageous for pharmaceutical applications.

To couple PEG to a molecule such as a protein or a small drug molecule, it is necessary to use an "activated derivative" of the PEG having a functional group at the terminus suitable for reaction with a group on the other molecule. For example, the hydroxyl group of CH$_3$O-PEG-OH can be converted to an aldehyde group, and this aldehyde group can then be covalently linked to a molecule or surface bearing one or more amine groups using the method of reductive amination. An example of this approach is described in U.S. Pat. No. 5,252,714 to Harris and Herati. Detailed investigation for the functionalization of polyethylene glycol reported by Zalipsky for preparation of conjugates, the use of PEG acetaldehyde has been limited by its high reactivity, which leads to condensation side reactions. (See reference published in Bioconjugate Chemistry, 6:150 (1995). Recently the synthesis of PEG bearing at one end aldehyde and other end free hydroxyl group has been reported by Nagasaki et.al published in Macromolecules 1998, 31, 1473 using the initiator bearing protected group such as 3,3-diethoxy propanol (acetal group) that can be converted to aldehyde by hydrolysis at pH 2–3. This procedure allow to synthesize quantitative functionalization PEG bearing one end with aldehyde and other end hydroxyl group.

Preparation of PEG baring carboxylic acid and a hydroxyl group can be achieved by the oxidation of aldehyde group. The selective oxidatation reaction of the aldehyde group are problematic when working with polyethylene oxide polymer bearing free hydroxyl group. Oxidation of such polymer results in a number of impurities and some time degradation of polymer chain, therefore, destroying the architecture. Zalipsky and Barany in J. of Bioactive and Compatible Polymers, 5, 227–231 (1990) describe preparation of the following heterofunctional PEG in which the polymer has a carboxymethyl group at one terminus and a hydroxyl group at the other terminus. There are several other reports on the synthesis of Heterofunctional PEGs using homotelechelic PEG as the starting material for example see U.S. Pat. No. 5,672,662. The synthetic methods, however, are complicated because they have to use several reaction steps to derivatize the PEG terminus. In addition, the efficiency for derivatizations is not very high, meaning that the resulting PEG is a partial mixture of starting homotelechelics and the resulting heterotelechelics.

To date, use of living anionic polymerization has been a successful method for the preparation of end-reactive polymers with theoretical functionalities, narrow molecular weight distribution, and controlled molecular weight. Reactions of the living polymer end-chain with a variety of electrophiles have been carried out to generate different functional groups. This is a particularly suitable way to effect chain end functionalization, given it generates stable polymer end chains once all the monomer is consumed. The existence of the functional end groups renders the polymer important for use in biological and pharmaceutical applications.

DETAILED DESCRIPTION OF THE INVENTION

A first object of the present invention is constituted by heterofunctional polyethylene glycol or polyethylene oxide represented by one of the formula I to IV defined as follows:

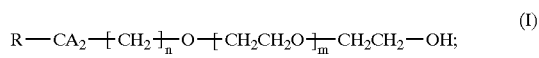

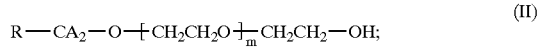

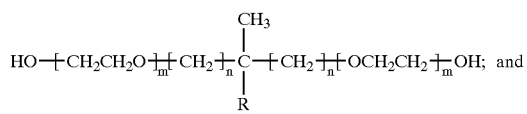

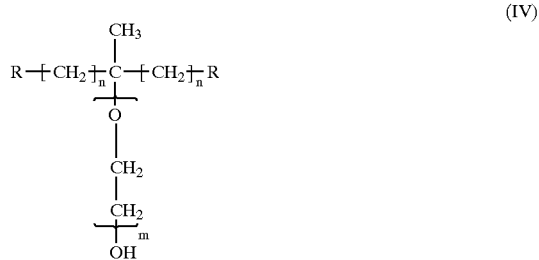

wherein:
- m is an integer from 5 to 10,000;
- n is an integer from 1 to 20;
- each R is independently an organic substituent, preferably a hydrocarbon substituent that preferably comprises at least one heteroatom,
- each A is independently an alkyl, a substituted alkyl group or a hydrogen atom, and the salts thereof.

According to a preferred embodiment of the invention the salts are selected in the group constituted by Li, Na, K and Cs, more preferably K.

According to another preferred embodiment of the invention, m is an integer from 5 to 10,000 more preferably m is about 50 and n is an integer from 1 to 20, more preferably n is about 3.

According to another preferred embodiment of the invention, R represents one of the following groups:
- COOX wherein X preferably represents an alkyl, a substituted alkyl group or a hydrogen atom;
- $COOSi(A)_3$ wherein each A preferably and independently represents an alkyl, a substituted alkyl group or a hydrogen atom;
- BCOONL, wherein B and L independently represent an alkyl, a substituted alkyl group or a hydrogen atom;

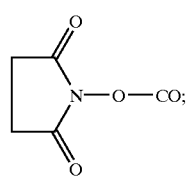

- an alkyl or a substituted alkyl group;
- COHal wherein Hal is a halogen atom;
- CONYZ wherein each of Y and Z preferably and independently represents an alkyl group or a substituted alkyl group or a hydrogen atom;
- $NX'Y'(CH_2)_nNZ'CO$ wherein each of X',Y', Z' preferably and independently represents an alkyl, a substituted alkyl group or a hydrogen atom;
- NX"Y" wherein each of X" and Y" preferably and independently represents an alkyl, a substituted alkyl group or a hydrogen atom;
- COOR' wherein R' preferably represents an alkyl, a substituted alkyl group or a hydrogen atom;
- NX'''Y''' wherein each of X''' and Y''' independently represents an alkyl group, a substituted alkyl group or a hydrogen atom.

According to a further preferred embodiment of the invention, the term "substituted" means substituted by an halogen atom, which is preferably a fluor atom.

The term "alkyl" preferably means a $C_1$ to $C_5$ alkyl group which is more preferably a methyl group, the term Hal means halogen preferably a fluor atom.

A second object of the present invention is constituted by the heterofunctional polyethylene glycol or polyethylene oxide containing at least one hydroxyl moiety and one carboxylic acid moiety obtainable by the process according to the invention thereafter defined.

A third object of the present invention is constituted by a process for producing heterofunctional polyethylene glycol or polyethylene oxide containing at least one hydroxyl moiety and one carboxylic acid moiety by means of living anionic polymerization, which process comprises the steps of:
i) activating a monomer with an initiator which is an organic molecule that comprises at least one COOM function wherein, in the OM moiety, M represents an alkaline metal;
ii) polymerising the initiated molecules obtained in the preceding step preferably under an inert atmosphere; and
iii) terminating the polymerization step by adding an acid.

According to another preferred embodiment of this process in item i) the monomer which is activated is selected in the group constituted by alkylene oxides such as an ethylene oxide, a propylene oxide or a butylenes oxide and by macrocyclic esters such as glycolide, lactide or lactone with an initiator which is an organic molecule that comprises at least one COOM function wherein, in the OM moiety, M is selected in the group constituted by Li, Na, K or Cs;

In item ii) the initiated molecules obtained in the preceding step i) are polymerized preferably under an inert atmosphere and in a solvent;

The termination of the polymerization step is terminated by adding an acid, which is selected in the group constituted by the acetic acid, the dichloroacetic acid, and the hydrochloric acid.

According to a further preferred embodiment of the invention in step ii) the solvent is selected in the group constituted by water, the tetrahydrofuran, the dioxane, the N,Ndimethyl formamide, the dimethylsulfoxide, the ethylene glycol dimethylether and mixtures thereof, and more preferably the tetrahydrofuran.

According to another preferred embodiment of this invention the monomer in step i) is the ethylene oxide and the initiator is preferably an organic molecule with a COOK moiety.

The polymerization in step ii) is preferably carried out at about 50° C. in presence of tetrahydrofuran.

The termination in step iii) is preferably carried out by adding acetic acid.

The process according to the invention is preferably a one batch process.

A fourth object of the present invention is constituted by a solution of at least one heterofunctional polyethylene glycol or polyethylene oxide containing at least one hydroxyl moiety and one carboxylic acid moiety according to the first and to the second object of the present invention with an organic solvent.

The organic solvent is preferably selected in the group constituted by water, the tetrahydrofuran, the dioxane, the N,Ndimethyl formamide, the dimethylsulfoxide, the ethylene glycol dimethylether and mixtures thereof. The organic solvent is more preferably tetrahydrofuran.

The amount of solvent in the solution is preferably comprised between 10 and 90 weight per cent, and is more preferably about 70 weight per cent.

A fifth object of the present invention is constituted by the use of a solution according to the fourth object of the present invention to form conjugates by reductive amination with a range of biologically active molecules which are preferably proteins, peptides, polysaccharides, oligonucleotides or small drug molecules.

A sixth object of the present invention is constituted by the use of the above defined heterofunctional polyethylene glycol or polyethylene oxide as carriers for drug delivery or as diagnostic reagents.

Our strategy for heterotelechelic polymer synthesis is starting from a anionic living polymerization of ethylene oxide (EO) using new initiators containing defined functionalities. PEG polymers of the invention should be substantially non-toxic and should not tend substantially to produce an immune response or cause clotting or other undesirable effects.

The said invention provides a simplified one step procedure for the commercial production of PEG containing either one hydroxyl or two hydroxyl groups with one or two carboxylic acid groups per molecule of polyethylene glycol. The obtained polymer bears the quantitative functionalization with the required architecture with controlled molecular weight. Since the process is the living anioinic ring opening polymerization the molecular weight of the polymer can be controlled and is based on the monomer over initiator molar ratio (theoretical molecular weight $Mn=44[M]o/[I] \times \%$ conversion of the monomer, [M]o and [I] is the molar ratio of monomer vs. initiator. The molecular weight of the obtained polymer is fairly narrow $Mw/Mn<1.3$. The reaction is completed over 80% conversion of monomer in 4–5 h at 40–50° C. reaction temperature if one is targeting molecular weight of the polymer below 30,000 g/mol. The polymerization was carried out using potassium counter ion based initiator in tetrahydrofuran (THF). The polymerization was carried out using potassium based catalyst under agron inert atmosphere. Polymer chain having at least one free carboxylic acid functional group and the polymer can be isolated with substantial high purity. Drying and removal of the solvent is done by distillation in an inert atmosphere. The obtained polymer is stored in the cold under an inert atmosphere. These polymers can be used in solution, to form conjugates by reductive amination with a range of biologically active molecules, including proteins, peptides, polysaccharides, oligonucleotides, and small drug molecules. Examples of suitable polymer forms include but are not limited to linear or branched or dendritic or star structures, degradable structures, hydrogel forming structures, and others. Other suitable polymers include other poly(alkylene oxides) such as poly(propylene glycol) ("PPG"). The starting PEG polymer molecule has at least one carboxylic acid moiety and one hydroxyl moiety. These functional groups are available to participate in chemical reactions and are considered to be an active groups. The PEG molecule can also have multiple active carboxylic acid available for chemical reactions. PEG typically has average molecular weight of from 200–100,000 and its biological properties can vary with molecular weight so not all of these derivatives may be useful for biological or biotechnical applications. For many biological and biotechnical applications, substantially linear, straight-chain PEG containing at least one carboxylic acid and one hydroxyl is useful. These bifunctional PEG beraing heterofunctional group can be used to cross-linked biological materials such as proteins, aminopolysacchrides such as chitosan to form hydrogel.

The following examples are given by way of illustration and do not limit the present invention.

EXAMPLE 1 (LOG BOOK #P2243)

Preparation of α-carboxylic-ω-hydroxyl polyethylene oxide $$HOOC-(CH_2)_3-O-(CH_2CH_2O)_n-CH_2CH_2OH$$

Intitiator: 4-hydroxy butyric acid-sodium/potassium salt

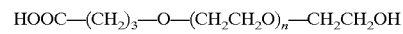

Synthesis of the polymer is involved three steps: (1) Initiation of ethylene oxide monomer (2) Propagation of ethyene oxide monomers and (3) termination of polymerization.

Polymerization of ethylene oxide was carried out in a high pressure reactor (Par reactor) equipped with a magnetic driven mechanical stirrer. The reactor was bubbled with dried argon.

Initiator was prepared separately in a three necked 1 L flask equipped with magnetic stirrer and a condenser with three way stopcock. 4-hydroxy butyric acid-sodium salt (5.7 g 0.045 mol) obtained from Fluka Chemical Co was used as received (it contain <0.5% water) added to the flask followed by addition of freshly cut potassium (1.8 g 0.046 mol). After addition of the solid content the flask was evacuated followed by pressurizing (30 psi) with argon. Dried tetrahydrofuran (THF) 400 ml was added and the solution was refluxed for 12 h. A heterogeneous solution is formed. This solution was transferred to high pressure Par reactor under a flow of argon using 12 gauge double tip stainless steel needle. The reactor temperature was lowered to −10° C. Freshly distilled ethylene oxide (50 ml) (distilled over n-butyllithium) was added using stainless steel capillary. The solution was stirred at 50° C. for 24 h. The reactor temperature cool to water bath temperature and the reactor content was poured into a glass beaker containing HCl (5 ml of 35% aqueous solution). A slight yellow color solution is formed with the precipitation of salt (KCl). Solution was filtered and the filtrate precipitated in cold 2-propanol containing 20% hexanes, giving the desired product as a light yellow precipitate which is dried in vacuo overnight. Yield 38 g (86.3%).

In an Erlenmeyer flask equipped with a magnetic stir bar, obtained polymer from the preceding step was added to 500 ml distilled deionized water and stirred to dissolve followed by addition of dichloromethane to extract the polymer and to remove the unreacted initiator and residual amount of salt present. The solution was washed with deionized water two times than the dichloromethane solution was concentrated in rotavapor. The product finally reprecipitated in cold diethyl ether. The product was dried in vacuo overnight. Yield: g, 88%. $^1$H-NMR (CDCl$_3$) 2.35 ppm (m, —CH2 2H adjacent to COOH), 3.60 ppm (s, PEG backbone, 77H), 4.37 ppm (t, OH, 1H). $^1$H NMR spectrum is reported in FIG. 1.

Size exclusion chromatography (SEC) was carried out on a Varian liquid chromatograph equipped with a refractive detector. Three columns from Supelco (G6000-4000-2000 HXL) were used with THF as the eluent. The columns were calibrated with monodisperse polyethylene glycol standards. The molecular weight and the polydispersity indice were calculated. The SEC analysis of the product indicating Mn of 440 MwMn 1.16. The SEC trace is reported in FIG. 2. The value calculated from H NMR indicates Mn 1070. This indicating some interaction of the heterofunctional PEG with the packing materials of the column that resulting the retardation of the elution therefore underestimating the molecular weight of the polymer. FTIR spectrum of the resulting product is shown in FIG. 3 clearly indicating the presence of COOH end functional group (characteristic absorbance at 1738 cm$^{-1}$). Degree of carboxylic acid functionality was determined by acid base titration by dissolving polymer in de-ionized water and titration against 0.25 normality NaOH and using phenolphthalein as indicator. The carboxylic acid functionality was found 0.98.

EXAMPLE 2 (LOG BOOK #P2259)

Preparation of a α-carboxylic ω-hydroxyl polyethylene oxide

HOOC—(CH$_2$)$_3$—O—(CH$_2$CH$_2$O)$_n$—CH$_2$CH$_2$OH

Intitiator: 4-hydroxy butyric acid-sodium/potassium salt

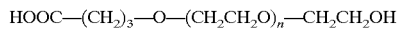

Polymerization of ethylene oxide was carried out as outlined in example 1. Initiator was based on potassium alcoholate of 4-hydroxy butyric acid sodium salt. 4-hydroxy butyric acid (4.2 g 0.033 mol) was stirrered in dried tetrahydrofuran (THF) 400 ml and the solution was brought to 40° C. and the solution was treated with potassium 1.3 g (0.033 mol) the solution was refluxed for 12 h. A heterogeneous solution is formed. This solution was transferred to high pressure Par reactor under a flow of argon using 12 gauge double tip stainless steel needle. The reactor temperature was lowered to -10° C. Freshly distilled ethylene oxide(80 ml 70 g) (distilled over n-butyl lithium) was added using stainless steel capillary. The solution was stirrer at 50° C. for 24 h. The reactor temperature cool to water bath temperature and the reactor content was poured into a glass beaker containing HCl (5 ml of 35% aqueous solution). A slight yellow color solution is formed with the precipitation of salt (KCl). Solution was filtered and the filtrate precipitated in cold 2-propanol containing 20% hexanes, giving the desired product as a light yellow precipitate which is dried in vacuo overnight. Yield 40 g (57%). Molecular weight determined by SEC Mn 850 Mw/Mn 1.39 (Mn from H NMR 1400).

EXAMPLE 3 (LOG BOOK #P2264)

Mn determined by acid base titration was found to be 1600.
Intitiator: 4-hydroxy butyric acid-sodium/potassium salt
Preparation of α-carboxylic ω-hydroxyl polyethylene oxide HOOC—(CH$_2$)$_3$—O—(CH$_2$CH$_2$O)$_n$—CH$_2$CH$_2$OH Polymerization of ethylene oxide was carried out as outlined in example 1. Initiator was based on potassium alcoholate of 4 hydroxy butyric acid sodium salt. 4-hydroxy butyric acid (4.2 g 0.033 mol) was stirrer in dried tetrahydrofuran (THF) 400 ml mixed with 18 crown ether 6 (8.7 g 0.033 mol) and potassium (1.3 g 0.033 mol) and the solution was brought to 40° C. and stirrer. A deep violet blue color is formed and disappeared simultaneously. Finally a heterogeneous solution is formed and potassium metal completely disappeared. This solution was transferred to high pressure par reactor under a flow of argon using 12 gauge double tip stainless steel needle. The reactor temperature was lowered to -10° C. Freshly distilled ethylene oxide (95 ml 83.6 g) (distilled over n-butyl lithium) was added using stainless steel capillary. The solution was stirrer at 50° C. for 24 h. The reactor temperature cool to water bath temperature and the reactor content was poured into a glass beaker containing HCl (5 ml of 35% aqueous solution). A slight yellow color solution is formed with the precipitation of salt (KCl). Solution was filtered and the filtrate precipitated in cold 2-propanol containing 20% hexanes, giving the desired product as a light yellow precipitate which is dried in vacuo overnight. Yield 76 g (91%). Molecular weight determined by SEC Mn 4000 Mw/Mn 1.17 (Mn determined by acid base titration 4500). The SEC of the product is illustrated in FIG. 4. FT-IR spectrum of the product is illustrated in FIG. 5.

EXAMPLE 4 (LOG BOOK #P2263)

Preparation of α-carboxylic ω-hydroxyl polyethylene oxide (extension of molecular weight from the low molecular weight heterofunctional PEG)

HOOC—(CH$_2$)$_3$—O—(CH$_2$CH$_2$O)$_n$—CH$_2$CH$_2$OH

Polymer prepared in example 1 was taken in a three neck 1000 ml round bottom flask equipped with a magnetic stir bar, a Dean-Stark trap, a reflux condenser and a drying tube filled with CaCl$_2$. Polymer (25.0 g) was dissolved in 100 ml toluene. The mixture was azeotropically dried at 130° C. for approximately 30 minutes. About 40 ml cloudy solution (solvent/water) collected in the Dean-Stark trap. After draining the Dean-Stark trap, toluene was removed under reduced pressure and THF 500 ml was charged to the reactor. The flask was disconnected from the condenser and the Dean-Stark trap and replaced by stopper. The solution was titrated with 0.5M solution of potassium naphthalene. This requires 95 ml of 0.5M solution to get light green color. 5 ml more K-naphthalene was added to get the solution dark persistent green color. The solution becomes heterogeneous and the viscous mass separated out. Freshly distilled ethylene oxide (36 g 42 ml) was added and the polymerization was carried out at 40° C. for 24 h. Polymer recovered as outlined in example 1. Yield 60 g, 100%.

The isolated product was checked by NMR to confirm the architecture. Molecular weight determined by SEC Mn 2100 Mw/Mn 1.18 (Mn determined by acid base titration 3800 and by $^H$ NMR 4100). The SEC of the product is illustrated in FIG. 6. H NMR and FT-IR spectra of the product is illustrated in FIGS. 7 and 8 respectively.

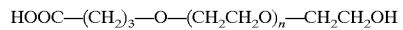

EXAMPLE 5 (LOG BOOK #2243)

Synthesis of α-hydroxy-ω.-succinimidyl-PEG

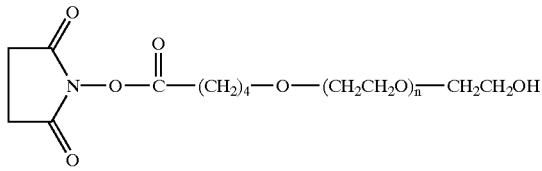

In a round bottom flask equipped with a magnetic stir bar and three way stop cock with rubber septum, attached to a nitrogen line and a bubbler, HO-PEG-COOH from the preceding step (10.00 g; 0.011 mol), N,N'-dicyclohexyl carbodiimide (1.5.times.excess; 3.64 g; 0.0176 mol) and N-hydroxysuccinimide (1.5.times.; 2.03 g; 0.0176 mol) were dissolved in 150 ml dichloromethane. The flask was kept at room temperature and the solution stirrer overnight. A cloudy heterogeneous white in color precipitated out. The reaction mixtures filtered, and the filtrate concentrated under reduced pressure, filtered and precipitated into cold diethyl ether and finally the resultant solution crystalized from dried ethanol. Yield 10.2 g, $^1$H NMR (CdCl$_3$) 2.45 ppm (m, CH2, 2H), 2.75 ppm, (s, succinimide, 4H), 3.50 ppm (s, PEG backbone, 77H), 4.60 ppm (t, OH, 1H).

EXAMPLE 6 (LOG BOOK #P2418)

Preparation of α-carboxylic ω-hydroxyl polyethylene oxide

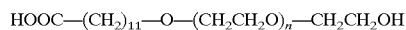

Here the polymerization was carried out in a glass reactor. Initiator was based on potassium alcoholate of 12-hydroxydodecanoic acid (97% purity from Aldrich Co. lot #03820PR) used as received. 12-hydroxydodecanoic acid (2.7 g 0.012 mol) was dissolved in dried tetrahydrofuran (THF) 150 ml and the solution was brought to 40° C. followed by titrating the solution with 0.5M solution of potassium naphthalene. 50 ml of 0.5M of K-naphthalene was used to get light green color solution. The solution slowly turns to a cloudy solution. The reactor temperature was lowered to −10° C. Freshly distilled ethylene oxide (35 ml 31 g) (distilled over n-butyllithium) was added using stainless steel capillary. The solution was stirrer at 40° C. for 24 h. The reactor temperature cool to water bath temperature and the reactor content was poured into a glass beaker containing HCl (4 ml of 30% aqueous solution). A clear solution is formed with the precipitation of salt (KCl). Solution was filtered and the filtrate precipitated in cold 2-propanol containing 20% hexanes, giving the desired product as a light yellow precipitate which is dried in vacuo overnight. Yield 31 g (95%). Molecular weight determined by SEC Mn 2000 Mw/Mn 1.16. The SEC analysis of the polymer also shows another species at higher molecular weight side. This fraction is around 12% calculated on the basis of SEC traces area. The molecular weight of this high molecular weight species are Mn 4500 Mw/Mn 1.2 ($^1$H-NMR (CDCl$_3$) 2.35 ppm (m, —CH2 2H adjacent to COOH), 3.60 ppm (s, PEG backbone, 248H), 1.37 ppm (CH2 of dodecanoic acid moiety 18H). Mn calculated by H NMR: 2730. The SEC of the product is illustrated in FIG. 9. H NMR and FT-IR spectra of the product is illustrated in FIGS. 10 and 11 respectively.

EXAMPLE 7 (LOG BOOK #P2420)

Preparation of α-carboxylic ω-hydroxyl polyethylene oxide

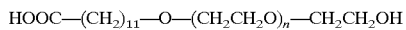

The polymerization was carried out in a glass reactor as in example #6. Initiator was based on potassium alcoholate of 12-hydroxydodecanoic acid (97% purity from Aldrich Co. lot #03820PR) used as received. 12-hydroxydodecanoic acid (2.2 g 0.0108 mol) was dissolved in dried tetrahydrofuran (THF) 150 ml and the solution was brought to 40° C. followed by titrating the solution with 0.5M solution of potassium naphthalene. 40 ml of 0.5M of K-naphthalene was used to get light green color solution. The solution slowly turns to a cloudy solution. The reactor temperature was lowered to −10° C. Freshly distilled ethylene oxide (47 ml 40 g) (distilled over n-butyllithium) was added using stainless steel capillary. The solution was stirrer at 40° C. for 24 h. The reactor temperature cool to water bath temperature and the reactor content was poured into a glass beaker containing HCl (4 ml of 35% aqueous solution). A clear solution is formed with the precipitation of salt (KCl). Solution was filtered and the filtrate precipitated in cold 2-propanol containing 20% hexanes, giving the desired product as a light yellow precipitate which is dried in vacuo overnight. Yield 35 g (83%). Molecular weight determined by SEC Mn 2000 Mw/Mn 1.21. The SEC analysis of the polymer also shows another species at higher molecular weight side. This fraction is around 24% calculated on the basis of SEC traces area. The molecular weight of this high molecular weight species are of Mn 12500 Mw/Mn 1.18 ($^1$H-NMR (CDCl$_3$) 2.35 ppm (m, —CH2 2H adjacent to COOH), 3.60 ppm (s, PEG backbone, 182H), 1.37 ppm (CH2 of dodecanoic acid moiety 18H). Mn calculated by H NMR: 2030. The SEC of the product is illustrated in FIG. 12. FT-IR spectra of the product is illustrated in FIG. 13.

EXAMPLE 8 (LOG BOOK #P2423)

Preparation of α-carboxylic ω-hydroxyl polyethylene oxide

The polymerization was carried out in a glass reactor as in example #6. Initiator was based on potassium alcoholate of 6-hydroxycaporic acid (from Aldrich Co. lot #13727EU) used as received. This compound containing up to 25% of the corresponding dimer lactone. 6-hydroxycaporic acid (1.0 g, 7.56 mmol) was dissolved in dried tetrahydrofuran (THF) 150 ml and the solution was brought to 40° C. followed by titrating the solution with 0.5M solution of potassium naphthalene. 35 ml of 0.5M of K-naphthalene was used to get light green color solution. The solution slowly turns to a cloudy solution. The reactor temperature was lowered to −10° C. Freshly distilled ethylene oxide (25 ml 22 g) (distilled over n-butyllithium) was added using stainless steel capillary. The solution was stirrer at 40° C. for 24 h. The reactor temperature cool to water bath temperature and the reactor content was poured into a glass beaker containing HCl (2 ml of 35% aqueous solution). A clear solution is formed with the precipitation of salt (KCl). Solution was filtered and the filtrate precipitated in cold 2-propanol containing 20% hexanes, giving the desired product as a light yellow precipitate which is dried in vacuo overnight. Yield 23 g (88%). Molecular weight determined by SEC indicating bimodal distribution. Mn of the low molecular weight species are of Mn 2370 and Mw/Mn of 1.24. The higher molecular weight species are of Mn 7800 and Mw/Mn of 1.07. This fraction is around 40% calculated on the basis of SEC traces area. The formation of high molecular weight fraction may due to the presence of 25% corresponding dimer in the starting material used as initiator. The SEC of the product is illustrated in FIG. 14.

EXAMPLE 9 (LOG BOOK #P2622)

Preparation of α-carboxylic ω-hydroxyl polyethylene oxide

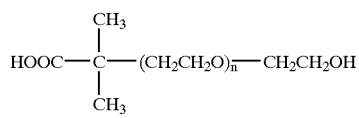

The polymerization was carried out in a glass reactor as in example #6. Initiator was based on potassium carbanions of tert.butylisobutyrate. tert.butyl isobutyrate was synthesized by reacting potassium tert.butanolate with isobutyrl chloride as shown schematically:

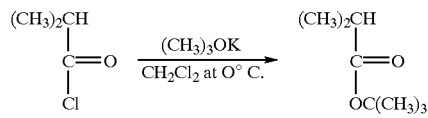

tert.butylisobutyrate (2 g, 0.014 mol) was dissolved in dried tetrahydrofuran (THF) 250 ml and the solution was brought to 40° C. followed by titrating the solution with 0.5M solution of triphenylmethyl potassium solution. 30 ml of 0.5M of triphenylmethyl potassium was used to get light reddish pink color solution. The solution was homogeneous. The reactor temperature was lowered to −10° C. Freshly distilled ethylene oxide (16 ml 14.1 g) (distilled over n-butyllithium) was added using stainless steel capillary. The solution was stiffer at 40° C. for 24 h. The reactor temperature cool to water bath temperature and the reactor content was poured into a glass beaker containing dichloracetic acid (0.5 ml). A clear solution is formed with the precipitation of salt. Solution was filtered and the filtrate precipitated in cold 2-propanol containing 20% hexanes, giving the desired product as a light yellow precipitate which is dried in vacuo overnight. Yield 12 g (80%). Molecular weight determined by SEC indicating unimodal distribution and Mn of 1970 Mw/Mn 1.10. SEC trace is illustrated in FIG. 15. The resulting polymer was dissolved in THF and treated with aq HCl or acetic acid. The resulting product was analysed by FT-IR and H NMR. The H NMR spectrum of the product indicating the presence of tert.butyl group, resonance at 1.2 ppm (FIG. 16). The molecular weight determined from HNMR shows Mn of 1270.

EXAMPLE 10 (Log #2627)

Preparation of α-carboxylic ω-hydroxyl polyethylene oxide

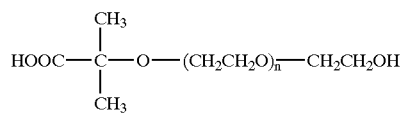

The polymerization was carried out in a glass reactor as in example #9. Initiator was based on potassium salt of 2 hydroxy butyric acid.

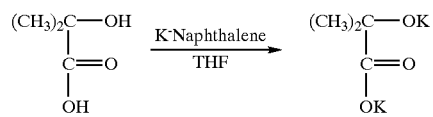

2-hydroxybutyric acid (1.0 g 0.009 mol) was dissolved in dried tetrahydrofuran (THF) 100 ml and the solution was brought to 40° C. followed by titrating the solution with 0.25M solution of potassium naphthalene solution. 80 ml of 0.25M of potassium naphthalene was used to get light green-pink color solution. The solution was heterogeneous. The reactor temperature was lowered to −10° C. Freshly distilled ethylene oxide (22.5 ml, 20 g) (distilled over n-butyllithium) was added using stainless steel capillary. The solution was stirrer at 40° C. for 24 h. The reactor temperature cool to water bath temperature and the reactor content was poured into a glass beaker containing 0.2 ml dichloro acetic acid. A clear solution is formed with the precipitation of salt. Solution was filtered and the filtrate precipitated in cold 2-propanol containing 20% hexanes, giving the desired product as a light yellow precipitate which is dried in vacuo overnight. Yield 7 g (35%). Molecular weight determined by SEC indicating unimodal distribution. Mn of 3910 Mw/Mn 1.24, the SEC analysis of the product is illustrated in FIG. 17. The product was analysed by FT-IR and H NMR analysis. The H NMR analysis indicating molecular weight of Mn 24000 and by acid base titration the carboxylic acid functionality was found around 30%.

EXAMPLE 11 (LOG BOOK #P2425)

Preparation of α-carboxylic ω-hydroxyl polyethylene oxide

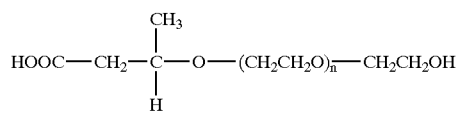

The polymerization was carried out in a glass reactor as in example #1. Initiator was based on potassium salt of 3-hydroxy butyric acid.

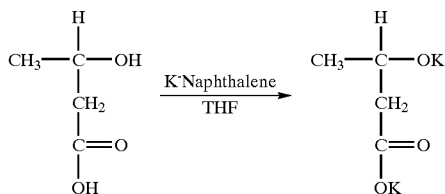

3-hydroxybutyric acid (2.5 g 0.024 mol) was dissolved in dried tetrahydrofuran (THF) 250 ml and the solution was brought to 40° C. followed by titrating the solution with 0.5M solution of potassium naphthalene solution. 100 ml of 0.5M of potassium naphthalene was used to get light green-pink color solution. The solution was heterogeneous and light yellow in color. This solution was transferred to high pressure Par reactor under a flow of argon using 12 gauge double tip stainless steel needle. The reactor temperature was lowered to −10° C. Freshly distilled ethylene oxide (40 ml 35.2 g) (distilled over n-butyllithium) was added using stainless steel capillary. The solution was stirrer at 50° C. for 48 h. The reactor temperature cool to water bath temperature and the reactor content was poured into a glass beaker containing HCl (5 ml of 35% aqueous solution). A slight yellow color solution is formed with the precipitation of salt (KCl). Solution was filtered and the filtrate precipitated in cold 2-propanol containing 20% hexanes, giving the desired product as a light yellow precipitate which is dried in vacuo overnight. Yield 34 g (96.5%).

Molecular weight determined by SEC indicating unimodal distribution with Mn of 2500 Mw/Mn 1.30. The SEC trace of the product is illustrated in FIG. 18. Mn by acid base titration indicates Mn of 4500 and by H NMR 3900. The H NMR spectrum of the product is illustrated in FIG. 19.

EXAMPLE 12 (LOG BOOK #P2625)

Preparation of α-ω dihydroxy polyethylene glycol bearing carboxylic acid functional moiety at the backbone of polymer chain

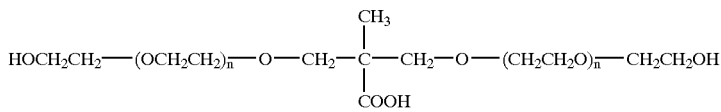

The polymerization was carried out in a glass reactor as in example #1. Initiator was based on potassium salt of 2,2-bis(hydroxymethyl)propionic acid. 2,2-Bis(hydroxymethyl)propionic acid (1.0 g 7.45 mmol) was dissolved in dried tetrahydrofuran (THF) 100 ml and the solution was brought to 40° C. followed by titrating the solution with 0.25M solution of potassium naphthalene solution. 100 ml of 0.25M of potassium naphthalene was used to get light green-pink color solution. The solution was heterogeneous and light pink in color. The reactor temperature was lowered to −10° C. Freshly distilled ethylene oxide (22.5 ml 20 g) (distilled over n-butyllithium) was added using stainless steel capillary. The solution was stirrer at 40° C. for 48 h. The reactor temperature cool to water bath temperature and the reactor content was poured into a glass beaker containing HCl (5 ml of 35% aqueous solution). A slight yellow color solution is formed with the precipitation of salt (KCl). Solution was filtered and the filtrate precipitated in cold 2-propanol containing 20% hexanes, giving the desired product as a light yellow precipitate which is dried in vacuo overnight. Yield 18 g (90%).

Molecular weight determined by SEC indicating unimodal distribution with Mn of 5000 Mw/Mn 1.10. The SEC trace of the product is illustrated in FIG. 20. Mn calculated from H NMR indicating the value of 6500. The H NMR spectrum of the product is illustrated in FIG. 21.

EXAMPLE 13 (LOG BOOK #P2625B)

Preparation of α,ω-dihydroxy polyethylene glycol bearing carboxylic acid functional moiety at the backbone of polymer chain

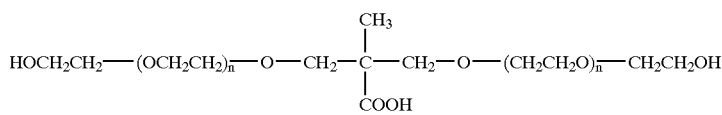

The polymerization was carried out in a glass reactor as in example #1. Initiator was based on potassium salt of 2,2-bis(hydroxymethyl)propionic acid. 2,2-Bis(hydroxymethyl)propionic acid (2.0 g 14.9 mmol) was dissolved in dried tetrahydrofuran (THF) 250 ml and the solution was brought to 40° C. followed by titrating the solution with 0.25M solution of potassium naphthalene solution. 200 ml of 0.25M of potassium naphthalene was used to get light green-pink color solution. The solution was heterogeneous and light pink in color. The reactor temperature was lowered to −10° C. Freshly distilled ethylene oxide (22.5 ml 20 g) (distilled over n-butyllithium) was added using stainless steel capillary. The solution was stirrer at 40° C. for 48 h. The reactor temperature cool to water bath temperature and the reactor content was poured into a glass beaker containing HCl (5 ml of 35% aqueous solution). A slight yellow color solution is formed with the precipitation of salt (KCl). Solution was filtered and the filtrate precipitated in cold 2-propanol containing 20% hexanes, giving the desired product as a light yellow precipitate which is dried in vacuo overnight. Yield 18 g (90%).

Molecular weight determined by SEC indicating unimodal distribution with Mn of 2200 Mw/Mn 1.10.

EXAMPLE 14 (LOG BOOK #P2644)

Preparation of α-α' dicarboxylic acid terminated polyethylene glycol

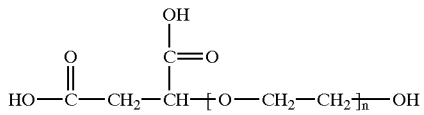

The polymerization was carried out in a glass reactor as in example #1. Initiator was based on potassium salt of DL-malic acid (DL-hydroxysuccinic acid). DL-malic acid (2.0 g 0.0149 mol) was dissolved in dried tetrahydrofuran (THF) 250 ml and the solution was brought to 40° C. followed by titrating the solution with 0.25M solution of potassium naphthalene solution. 200 ml of 0.25M of potassium naphthalene was used to get light green-pink color solution. The solution was heterogeneous and light pink in color. The reactor temperature was lowered to −10° C. Freshly distilled ethylene oxide. (22.5 ml 20 g) (distilled over n-butyllithium) was added using stainless steel capillary. The solution was stirrer at 40° C. for 48 h. The reactor temperature cool to water bath temperature and the reactor content was poured into a glass beaker containing HCl (10 ml of 35% aqueous solution). A slight yellow color solution is formed with the precipitation of salt (KCl). Solution was filtered and the filtrate precipitated in cold 2-propanol containing 20% hexanes, giving the desired product as a light yellow precipitate which is dried in vacuo overnight. Yield 12 g (74.5%). Molecular weight determined by SEC indicating unimodal distribution with Mn of 900 Mw/Mn 1.28.

We claim:

1. A heterofunctional polyethylene glycol or polyethylene oxide, and salts thereof, and wherein the polyethylene glycol or polyethylene oxide is represented by one of the formulas I to IV defined as follows:

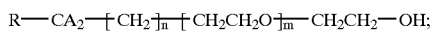 (I)

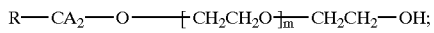 (II)

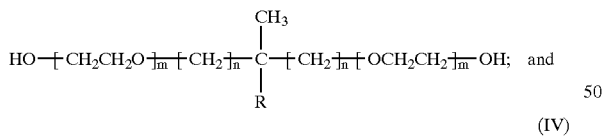 (III)

 and

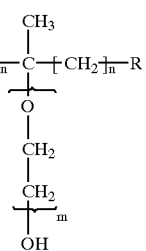 (IV)

wherein:
   m is an integer from 5 to 10,000;
   n is an integer from 1 to 20;
   each A is independently an alkyl, a substituted alkyl group or a hydrogen atom, and wherein for formulas (I), (III) and (IV), each R is independently an organic substituent, and optionally comprises at least one heteroatom, and wherein for formula (II), R represents one of the following groups:
   COOX, wherein X represents a substituted alkyl group when A is independently an alkyl, a substituted alkyl or a hydrogen, or wherein X represents an alkyl group when at least one A is an alkyl or substituted alkyl;
   $COOSi(A)_3$, wherein each A independently represents an alkyl, a substituted alkyl group or a hydrogen atom;
   BCOONL, wherein B and L independently represent an alkyl, a substituted alkyl group or a hydrogen atom;
   an alkyl or a substituted alkyl group;
   COHal, wherein Hal is a halogen atom;
   CONYZ, wherein each of Y and Z independently represents an alkyl group or a substituted alkyl group or a hydrogen atom;
   NX"Y", wherein each of X" and Y" independently represents an alkyl, a substituted alkyl group or a hydrogen atom;
   $(CH_2)_pCOOH$, wherein p=4–10
   $(CH_2)_2COOH$ or COOH when at least one A is an alkyl or substituted alkyl

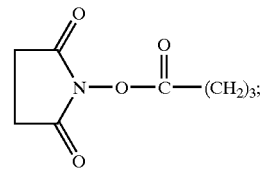

with the proviso that in formula (I), when each A represents a hydrogen atom, n is an integer from 3 to 20.

2. The heterofunctional polyethylene glycol or polyethylene oxide according to claim 1, wherein the salts are at least one member selected from the group consisting of Li, Na, K and Cs salts, and m is an integer from 5 to 10,000, and n is an integer from 1 to 20.

3. The heterofunctional polyethylene glycol or polyethylene oxide according to claim 1, wherein, for formulas (I), (III) and (IV), R represents one of the following groups:
   COOX, wherein X represents an alkyl, a substituted alkyl group or a hydrogen atom;
   $COOSi(A)_3$, wherein each A independently represents an alkyl, a substituted alkyl group or an hydrogen atom;
   BCOONL, wherein B and L independently represent an alkyl, a substituted alkyl group or a hydrogen atom;

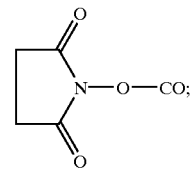

an alkyl or a substituted alkyl group;
COHal, wherein Hal is a halogen atom;
CONYZ, wherein each of Y and Z independently represents an alkyl group or a substituted alkyl group or a hydrogen atom;

NX"Y", wherein each of X" and Y" independently represents an alkyl, a substituted alkyl group or a hydrogen atom.

4. The heterofunctional polyethylene glycol or polyethylene oxide according to claim 3, wherein in the definition of formulas (I), (III) and (IV), the term substituted means substituted by an halogen atom, and wherein the term alkyl means a $C_1$ to $C_5$ alkyl group.

5. The heterofunctional polyethylene glycol or polyethylene oxide according to claim 4, wherein, in the definition of formulas (I), (III) and (IV), the terms Hal and halogen mean fluorine, and the term alkyl means methyl group.

6. A solution comprising at least one heterofunctional polyethylene glycol or polyethylene oxide containing at least one hydroxyl moiety and one carboxylic acid moiety, according to claim 1, and a solvent.

7. The solution according to claim 6, wherein the solvent is selected from water, tetrahydrofuran, dioxane, N,N-dimethyl formamide, dimethylsulfoxide, ethylene glycol dimethylether or mixtures thereof.

8. The solution according to claim 6, wherein the amount of solvent in the solution is between 10 and 90 weight per cent.

9. The solution according to claim 6, wherein the solvent is an aqueous solvent.

* * * * *